US009522027B2

(12) United States Patent  
Leuenberger et al.

(10) Patent No.: US 9,522,027 B2  
(45) Date of Patent: Dec. 20, 2016

(54) LASER TYPE FIXATION MEMBER SECUREMENT DEVICE AND ACTIVATION SYSTEM, AND RELATED SYSTEM AND METHODS

(71) Applicant: DePuy Synthes Products, Inc., Raynham, MA (US)

(72) Inventors: Samuel Leuenberger, Oberwil (CH); Dieter Schmidli, Seewen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/973,840

(22) Filed: Dec. 18, 2015

(65) Prior Publication Data

US 2016/0100869 A1    Apr. 14, 2016

Related U.S. Application Data

(62) Division of application No. 13/796,084, filed on Mar. 12, 2013, now Pat. No. 9,247,981.

(51) Int. Cl.
   *A61B 17/84*    (2006.01)
   *A61B 17/88*    (2006.01)
   *A61B 17/86*    (2006.01)

(52) U.S. Cl.
   CPC ............. *A61B 17/84* (2013.01); *A61B 17/844* (2013.01); *A61B 17/866* (2013.01); *A61B 17/8863* (2013.01)

(58) Field of Classification Search
   CPC .................... A61B 17/8863; A61B 2018/202; A61B 2017/00371; A61B 2017/005; A61B 2017/00508
   See application file for complete search history.

(56) References Cited

U.S. PATENT DOCUMENTS

| | | | |
|---|---|---|---|
| 4,422,457 | A | 12/1983 | Hattori |
| 4,561,440 | A | 12/1985 | Kubo et al. |
| 4,905,690 | A | 3/1990 | Ohshiro et al. |
| 5,012,087 | A | 4/1991 | Rockstroh et al. |
| 5,966,206 | A | 10/1999 | Jander |
| 6,285,693 | B1 | 9/2001 | Sagehashi |
| 6,724,958 | B1 | 4/2004 | German et al. |
| 2009/0143773 | A1 | 6/2009 | Gosse et al. |
| 2010/0241229 | A1 | 9/2010 | Baehre et al. |

(Continued)

FOREIGN PATENT DOCUMENTS

| | | | |
|---|---|---|---|
| EP | 2065017 A1 | 6/2009 | |
| WO | WO 01/50963 A1 | 7/2001 | |

(Continued)

OTHER PUBLICATIONS

U.S. Appl. No. 61/777,508, filed Mar. 12, 2013, Leuenberger et al.

*Primary Examiner* — Andrew Yang  
(74) *Attorney, Agent, or Firm* — Baker & Hostetler LLP

(57) ABSTRACT

A laser device having a proximal end and a distal end spaced from the proximal end, the distal end configured to receive a fixation member to be affixed to a target surgical site. The laser device includes a laser source supported by the laser device body and capable of emitting a laser beam to the distal end, wherein the laser source is responsive to at least one input so as to selectively switch between an inactive configuration whereby the laser source does not emit the laser beam, and an active configuration whereby the laser source emits the laser beam.

20 Claims, 17 Drawing Sheets

(56) References Cited

U.S. PATENT DOCUMENTS

| | | |
|---|---|---|
| 2011/0032960 A1 | 2/2011 | Gerlitz |
| 2011/0160870 A1 | 6/2011 | Baumgartner et al. |
| 2011/0245819 A1 | 10/2011 | Nardini et al. |
| 2012/0041557 A1 | 2/2012 | Frigg |
| 2012/0129131 A1 | 5/2012 | Baehre et al. |

FOREIGN PATENT DOCUMENTS

| | | |
|---|---|---|
| WO | WO 2009/003294 A1 | 1/2009 |
| WO | WO 2009/036576 A1 | 3/2009 |
| WO | WO 2012/087426 A1 | 6/2012 |

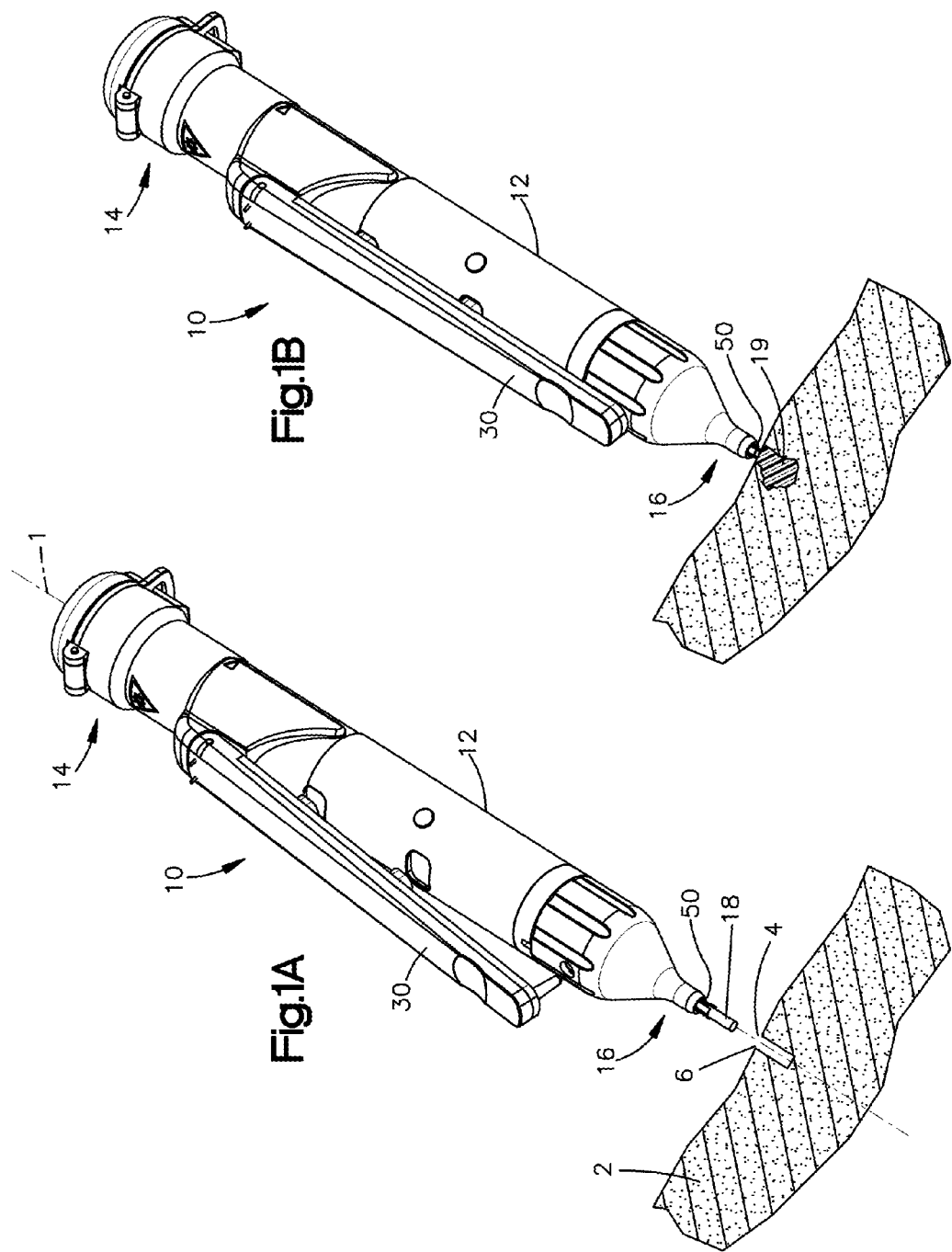

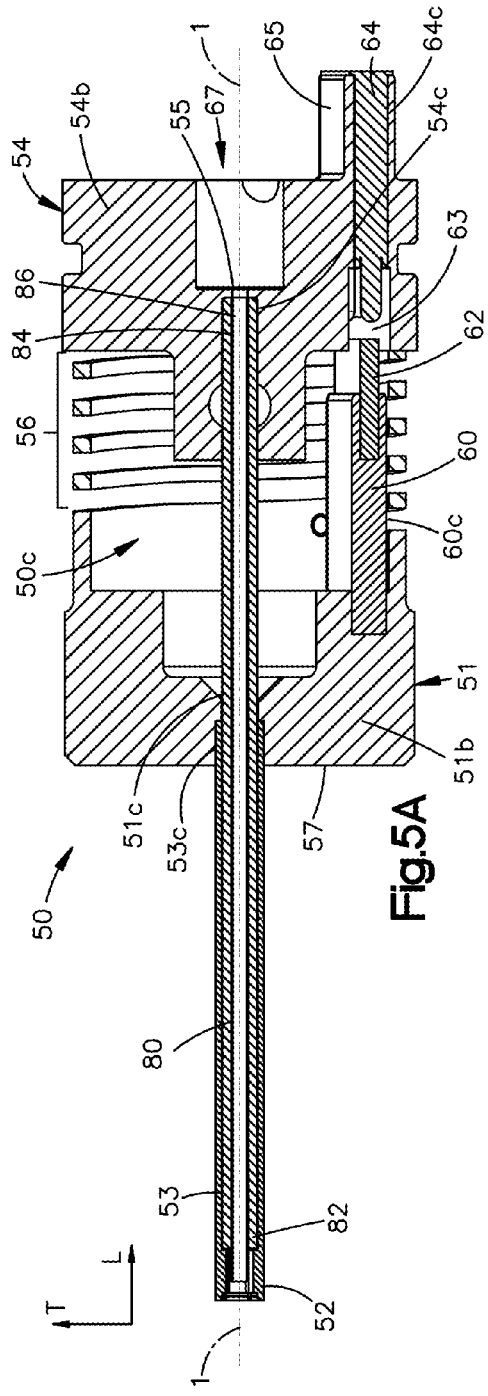
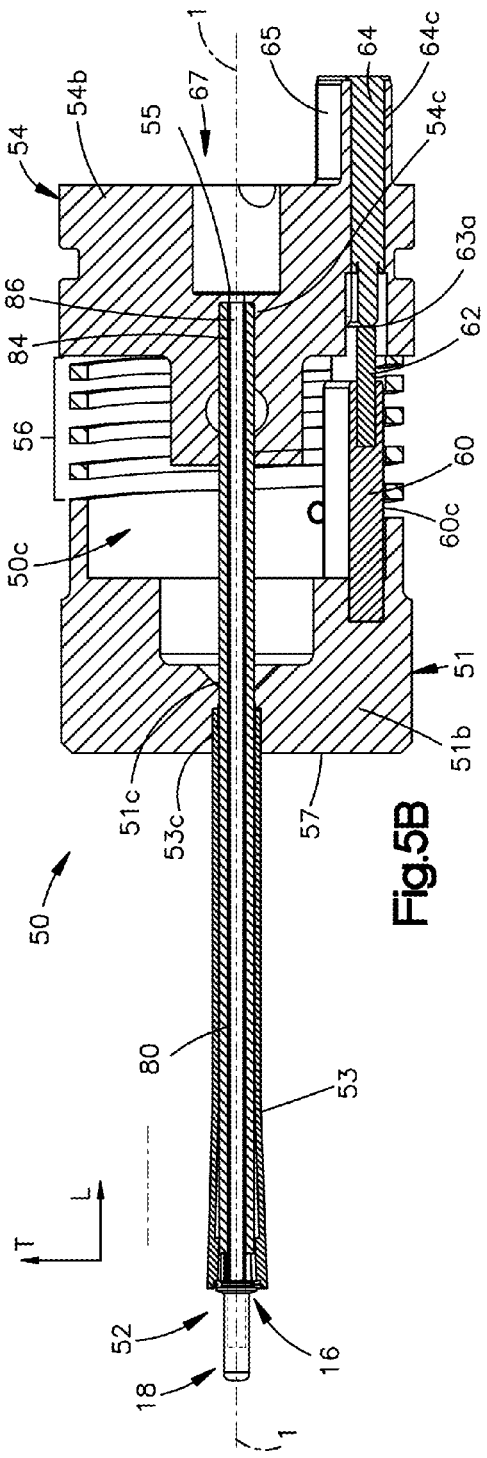
Fig.5A
Fig.5B

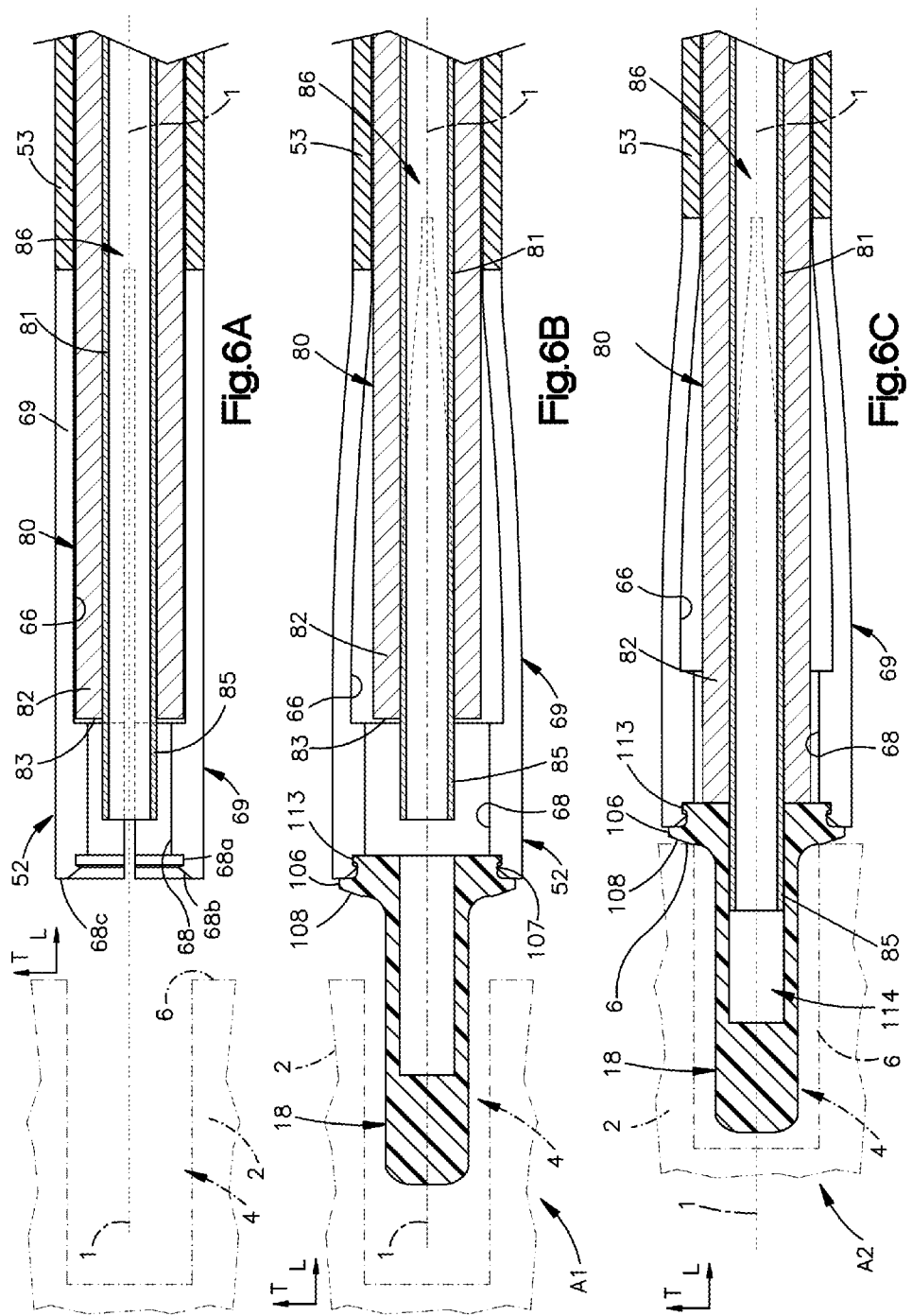

LASER TYPE FIXATION MEMBER SECUREMENT DEVICE AND ACTIVATION SYSTEM, AND RELATED SYSTEM AND METHODS

CROSS-REFERENCE TO RELATED APPLICATIONS

This application is a divisional application of U.S. patent application Ser. No. 13/796,084, filed Mar. 12, 2013, the disclosure of which is hereby incorporated by reference as if set forth in its entirety herein.

TECHNICAL FIELD

The present disclosure is directed to a laser-type fixation member securement device, fixation member system and method, and particularly to a system for activating a laser type fixation member securement device, system and method for securing a fixation member to tissue and/or an implant.

BACKGROUND

A surgeon selects a bone fixation procedure and the associated fixation member in light of a number of factors. A few important considerations include the indications presented by the trauma, procedural invasiveness, probable rate of tissue restoration, trauma location and accessibility, and instrumentation complexity. Sometimes procedural complexity alone could cause the surgeon exclude from consideration an otherwise viable fixation technique and type of fixation member.

Lasers are being increasingly used in surgery despite the complexity involved in using them. Because lasers are precise and only the affected or target areas are treated with the laser, trauma to unaffected tissues around the targeted area can be minimized, if not avoided altogether. Lasers also enable minimally invasive procedures, which reduces infection risk, pain, bleeding and/or swelling. These factors can improve patient outcomes and may lead to increased usage of lasers in surgery.

Lasers have drawbacks. There is a risk of injury to the user and patient if the laser is used improperly. To address this risk governmental agencies classify and impose strict protective measures on laser use. Although warranted, this regulatory framework increases surgical procedure complexity. One commonly used classification system—Standard IEC 60825-1 (incorporated by reference herein in its entirety)—categorizes lasers as either a Class 1, 2, 3, or 4 lasers. The level of protective measures (e.g. administrative controls, labeling, and use personal protective equipment (PPE)) varies with each class. Class 4 lasers, which are commonly used in medical applications, provide that users and people in close proximity to the laser beam during use to wear safety goggles, among other things. Lasers and their associated devices, though suitable to address many indications, are thus sometimes excluded from consideration because of the added complexity of using a laser beam in an operating room, e.g. goggle use, administrative burden, etc.

SUMMARY

An embodiment of the present disclosure includes a laser device having a proximal end and a distal end spaced from the proximal end, the distal end configured to receive a fixation member to be affixed to a target surgical site. The laser device includes a laser source supported by the laser device body and capable of emitting a laser beam to the distal end, wherein the laser source is responsive to at least one input so as to selectively switch between an inactive configuration whereby the laser source does not emit the laser beam, and an active configuration whereby the laser source emits the laser beam.

BRIEF DESCRIPTION OF THE DRAWINGS

The foregoing summary, as well as the following detailed description of illustrative embodiments of the laser device of the present application, will be better understood when read in conjunction with the appended drawings. It should be understood, however, that the application is not limited to the precise schematics and arrangements shown. In the drawings:

FIG. 1A is a perspective view of a laser device in an inactive configuration used to introduce a fixation member to a surgical site, according to an embodiment of the of the present disclosure;

FIG. 1B is a perspective view of a laser device in FIG. 1A in an activated configuration illustrating the fixation member disposed in and fixed at the surgical site;

FIGS. 5A and 5B are cross sections of the actuator assembly taken along line 5A-5A in FIG. 4, illustrating the actuator assembly in an inactive configuration and the active configuration, respectively;

FIG. 6A is a partial cross-sectional view of a fixation member receiving end of the actuator assembly shown in FIG. 5B, when the actuator assembly is in the first position;

FIG. 6B is a partial cross-sectional view of the fixation member receiving end of the actuator assembly shown in FIG. 5B, illustrating the actuator assembly in the actuated position with the fixation member received therein;

FIG. 6C is a partial cross-sectional view of the fixation member receiving end of the actuator assembly shown in FIG. 5B, illustrating the actuator assembly in the actuated position with the fixation member received therein and the fixation member inserted into the target surgical site (shown in dashed lines);

DETAILED DESCRIPTION OF ILLUSTRATIVE EMBODIMENTS

Figure 2A:
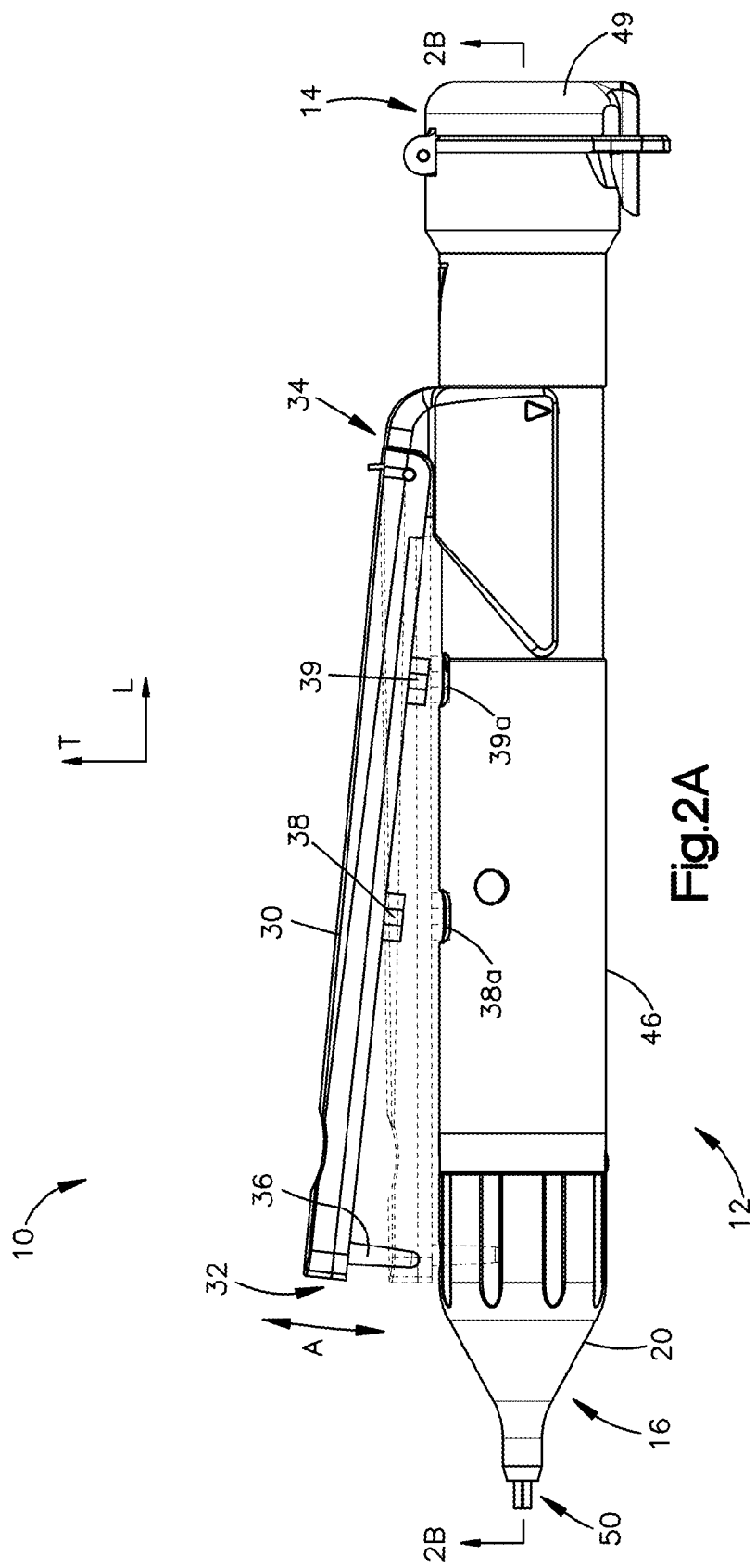
FIG. 2A is an elevation view of the laser device in FIGS. 1A and 1B, shown without a fixation member positioned on the laser device.

Referring initially to FIGS. 1A and 1B, a laser type fixation member securement device, or laser device 10 as used herein, includes a laser source 70 (FIG. 2D) operably connected to a power source. The laser device 10 can further include an activation system that is configured to selectively place the laser source 70 in electrical communication with the power source. Accordingly, the laser device 10 is capable of an inactive configuration, whereby the laser source 70 (FIG. 2D) housed in the laser device 10 is not operable to emit a laser, and an active configuration shown in FIG. 1B, whereby the laser source is operable to emit a laser. As illustrated, a fixation member 18 can be positioned in and supported by the laser device 10 for delivery to the desired surgical site, e.g., a bone 2. Thus, when the laser device 10 is in the active configuration, the laser source 70 can emit a laser beam into the fixation member 18 to soften or melt the fixation member 18. The softened fixation member 18 can be deformed into a securement 19 as shown in FIG. 1B.

FIGS. 1A and 1B illustrates the laser device 10 approaching a target surgical site, such as a bone 2 with a cavity 4 formed in the bone surface 6. The cavity 4 can be created prior to delivery of the fixation member 18 to the surgical site, or can be created during delivery of the fixation member to the surgical site. For instance, insertion of the fixation member 18 into the surgical site can create the cavity 4. Alternatively, the cavity 4 can be prepared using typical instruments for such purposes, such as a drill. The cavity 4 is sized to receive the fixation member 18. The surgical site can be a bone 2 as illustrated, though it should be appreciated that the surgical site can alternatively be any combination of a bone, soft tissue, a plate, netting, wire frame, rod, or any other device or fixation member that could be secured to bone or other tissue.

The laser device 10 is configured to allow a user to control power to the laser source 70, thereby controlling the emission of the laser beam therefrom. For instance, in one mode, the laser device 10 can prevent power from traveling from the power source to the laser source 70, thereby preventing the emission of the laser beam from the laser source 70. In another mode, the laser device 10 can allow power to travel from the power source to the laser source, thereby causing the laser source to emit the laser beam to the fixation member 18. In an embodiment, the laser device 10 includes a laser device body 12 (FIG. 1A-2D), at least one actuator assembly supported by the laser device body 12, one or more electronic circuits 300 (FIG. 8) that cooperate with the at least one actuator assembly to selectively permit power to be supplied from a power source 90 (FIG. 8) to the laser source 70.

The actuator assemblies or actuators as described herein are each movable between a first position and an actuated position. When at least one of the actuators are in the first position the laser device is in the inactive configuration, and when the actuators in their respective actuated positions, the laser device is in the active configuration and the laser source can emit a laser beam. In an embodiment the laser device body 12 can include a first actuator assembly or first actuator 50 (FIGS. 4-6C) and a second actuator assembly or second actuator 30 (FIG. 1A-2A). The words "first" and "second" are used for purposes of illustrating the actuators and do not imply a hierarchy of one actuator over the other. The first actuator assembly 50 includes a fixation member receiving end 52 (or receiving end 52) configured so that when the fixation member 18 is disposed in the receiving end 52, the actuator assembly 50 can move from the first position to the actuated position, which can permit the power source 90 to supply power to the laser source 70. The second actuator assembly 30 is also configured to selectively operably connect the power source 90 to the laser source 70 such that when the second actuator assembly 30 is in the first position (FIG. 1A) the power source is disconnected from the laser source 70, and when the second actuator assembly 30 is in the actuated position (FIG. 1B) the power source can supply power to the laser source 70.

Continuing with FIGS. 1A and 1B, the laser device body 12 has a proximal end 14, and a distal end 16 spaced apart from the proximal end 14 along a longitudinal axis 1. The longitudinal axis 1 can define a longitudinal direction L. A transverse direction T refers to direction that is perpendicular to the longitudinal direction L. A portion of the first actuator assembly 50 (FIG. 1A), for instance the actuation member receiving end 52, protrudes from the distal end 16 of the laser device body 12 to receive the fixation member 18. A second actuator assembly 30 extends from and is operably connected to the laser device body 12.

Referring to FIGS. 2A-2D, the laser device body 12 can further include at least one housing for supporting one or more actuator assemblies, the laser source 70, the power source 90, and the one or more circuits 300. In the embodiment shown, the laser device body 12 can include a first housing 20 and a second housing 46 connected to the first housing 20. The second housing 46 can be connected the first housing 20 with a latch ring member 25. The latch ring member 25 can be monolithic with the first housing 20 or second housing 46. While the laser device body 12 is shown formed of multiple housings 20 and 46 connected together with a latch ring member 25, the laser device body 12 can be an integrally formed structure configured to support the components of the laser device 10.

The first housing 20 has a distal end 22, and a trailing end 24 spaced apart from the distal end 22 along the longitudinal direction L. The first housing 20 further defines a housing body 128 that can define the inner cavity 27 configured to support a portion of the first actuator assembly 50. Further, the housing body 128 can define a longitudinal bore 21 that extends distally along the longitudinal direction L from the inner cavity 27 toward the distal end 16 of the laser device body 12. The bore 21 is sized to receive and support the actuation member 53 (FIG. 4) of the actuator assembly 50 so that the fixation member receiving end 52 protrudes from the distal end 22 of the first housing 20.

Figure 2B:
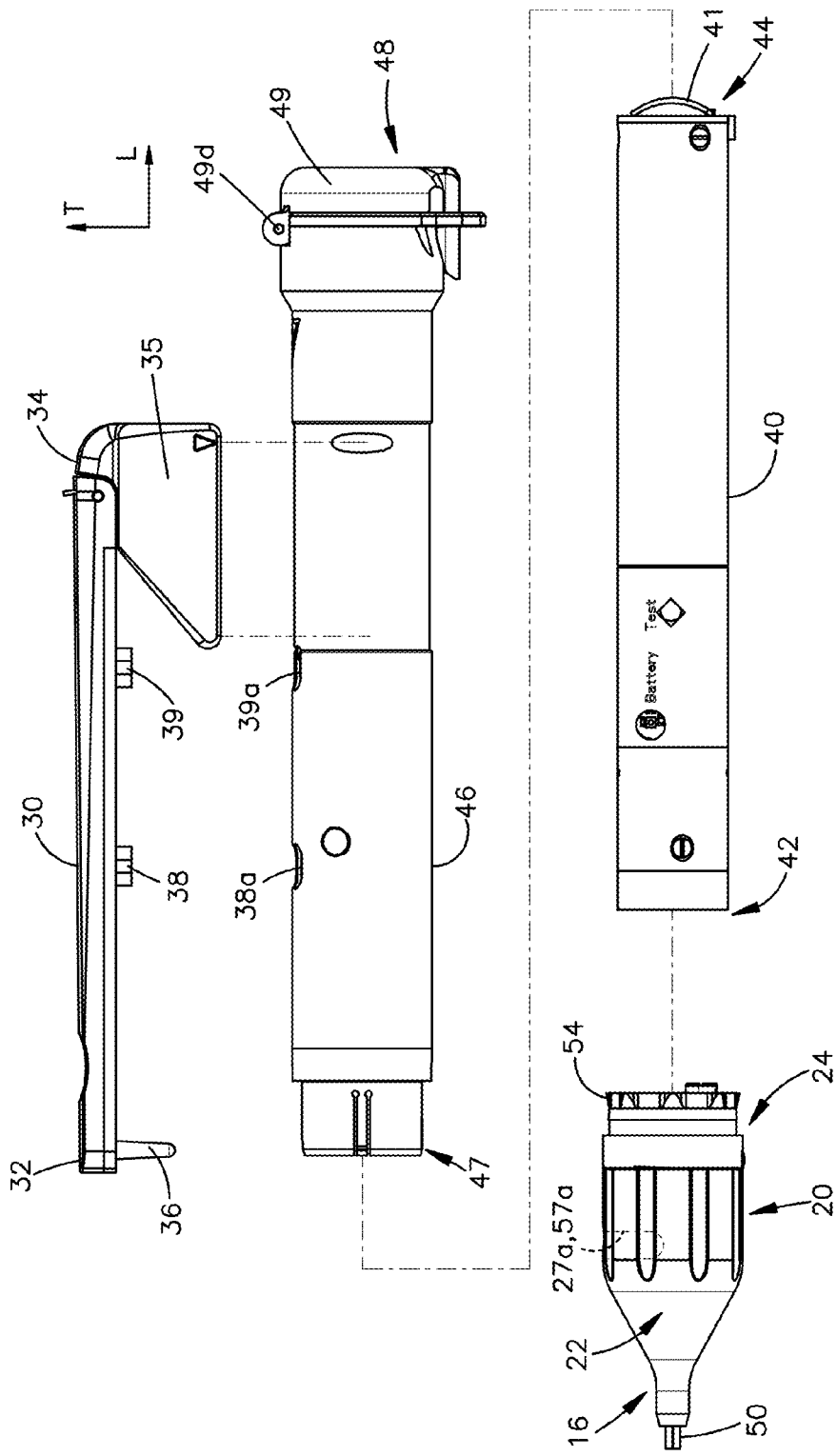
FIG. 2B is an exploded view of the laser device in FIG. 2A.
Figure 2C:
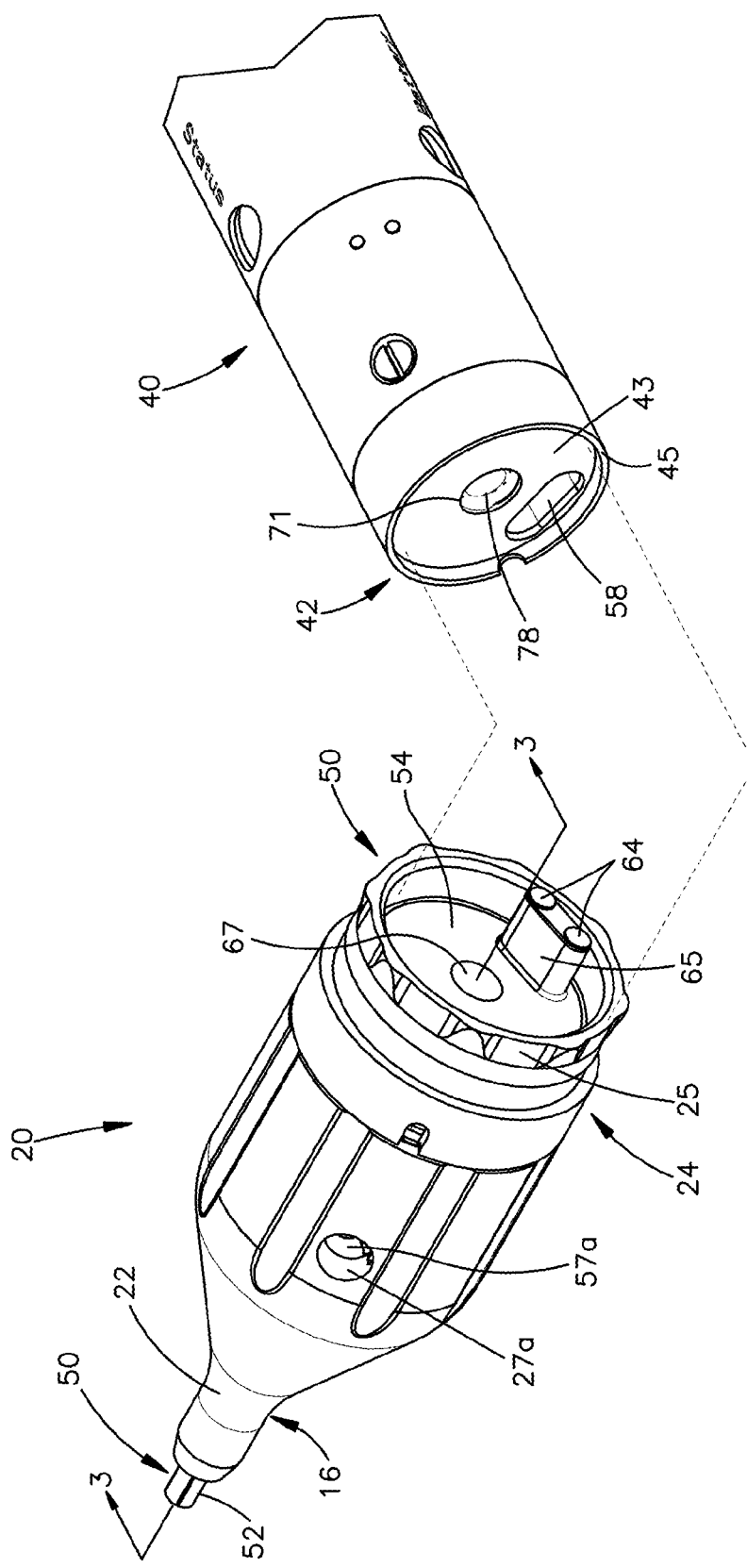
FIG. 2C is a detailed perspective exploded view of a portion of the laser device shown in FIG. 2B, illustrating how a laser device body engages with a laser cartridge.
Figure 2D:
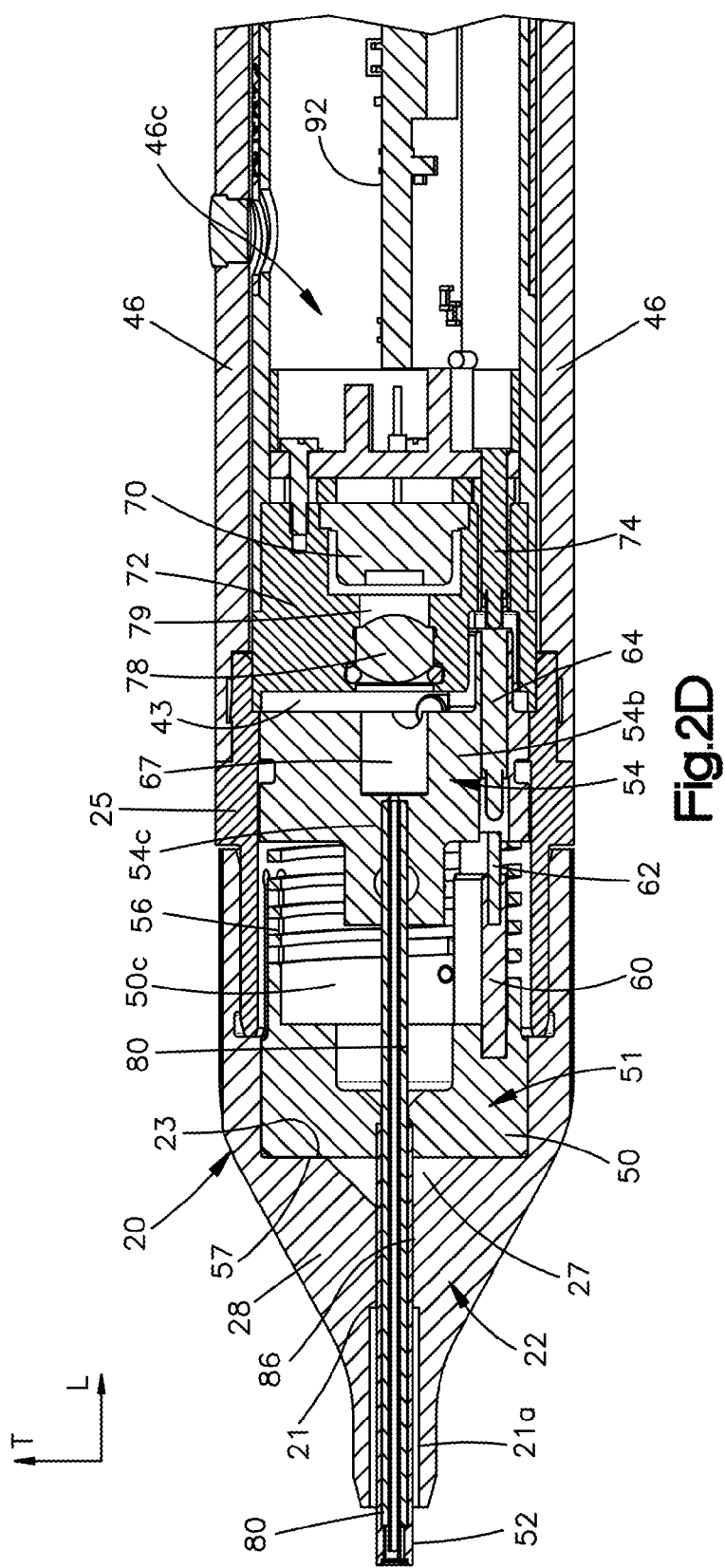
FIG. 2D is a partial cross-section of the laser device taken along the line 2D-2D shown in FIG. 2B.

As shown in FIG. 2B, the second housing 46 has a connecting end 47, and a proximal end 48 spaced apart from the connecting end 47 along the longitudinal direction L. The second housing 46 can define an inner cavity 46c for supporting therein a removable cartridge 40. As can be seen in FIG. 2D, the connecting end 47 can engage the latch ring member 25 (or trailing end 24) of the first housing 20. The proximal end 48, which can be the proximal end 14 of the laser device body 12, can be fitted with a moveable cap member 49 that can at least perform the function providing access to the cartridge 40 through the proximal end 14 of the laser device body 12.

In the illustrated embodiment, the cartridge 40 is configured to ensure a tight mechanical fit within the laser device body 12 as needed. The cartridge 40 can have a first end 42, and a second end 44 spaced apart from the first end 42 along longitudinal direction L. The second end 44 of the cartridge 40 can include a spring 41 (FIG. 2B) configured to operably engage with the moveable cap member 49 disposed on the device body 12. The cartridge 40 includes an inner cavity 46c supports the laser source 70, electronic circuitry 92, and a power source 90 or, for instance, an operable connection to a power source. The electronic circuitry 92 can include one or more circuits 300 physically arranged on a printed circuit board (PCB). When the cap member 49 is closed, the cap member 49 deflects the spring 41 to bias the cartridge 40 distally in the device body 12 ensuring a tight mechanical fit. It should be appreciated that the cartridge 40 can be integral or monolithic with first and second housings 20 and 46 of the laser device body 12, such that the cartridge body 72, laser source 70, electronic circuitry 92, and a power source 90 are supported directly by the laser device body 12.

Referring to FIG. 2D, the cartridge body 72 can be supported by the laser device body 12, for instance, disposed at least partially in the cartridge 40. The cartridge body 72 can define a distally facing end surface 43, and a ledge 45 extending distally along the longitudinal direction L. The cartridge body 40 further defines a distal opening 71 disposed at the surface 43 in alignment with the longitudinal axis 1, and a slot 58. The slot 58 is offset from the opening 71 and is configured to receive a portion of the actuator assembly 50. The cartridge body 72 further defines a bore 79 extending along the longitudinal direction L and through the body 72 into open communication with cartridge cavity 40c. The cartridge body 72 can further support a laser output mirror 78 disposed in the bore 79 and positioned toward the opening 71. The laser source 70 is positioned in the cavity 46c in axial alignment with a laser output mirror 78. The cartridge opening 71 is positioned to allow a laser beam to pass therethrough toward the distal end 16 of the laser device body 12.

Referring to FIGS. 2C, and 4-6C, the first actuator assembly 50 or first actuator is configured to selectively permit a power source 90 to supply power to the laser source 70. The first actuator assembly 50 is be movable between the first position illustrated in FIGS. 5A and 7A into the actuated position shown in FIGS. 5B and 7B. In accordance with the illustrated embodiment, the first actuator assembly 50 can include a base 54 that can be fixedly supported by the laser device body 12. For instance, the base 54 can be fixedly supported by the inner cavity 27 of the first housing 20 and stationary within the inner cavity 27. The actuator assembly 50 can include an assembly body 51 supported by the laser device body 12. For instance, the assembly body 51 is disposed and supported by inner cavity 27 of the first housing 20. The base 54 can further define a base body 54b. Further, the base body 54b can define an opening 67 with an aperture 55 disposed along distal face (not numbered) of the opening 67. The aperture 55 is aligned the laser source 70 (in the cartridge). The assembly body 51 can be spaced distally from the base 54 along the longitudinal direction L. The actuator assembly 50 can include a bias member 56, such as a spring, coupled between the assembly body 51 and base 54. The bias member provides a spring force that resists movement of the assembly body 50 along the longitudinal direction L toward the base 54. The actuator assembly 50 can further include an actuation member 53 projecting distally along the longitudinal direction L from the assembly body 51. The bias member 56 is configured to bias the actuation member 53 and the assembly body 51 distally into the actuated position shown in FIG. 5A.

The actuator assembly 50 can also include a pathway member 80 that is configured to guide a laser beam into the fixation member 18. At least a portion of actuator assembly 50 is slidable disposed along the pathway member 80. In the illustrated embodiment, the actuation member 53, the assembly body 51, and the base 54 are configured to support the pathway member 80. The pathway member 80 has a distal end 82 and a proximal end 84 spaced apart from the distal end 82 along the longitudinal axis L. A longitudinal bore 86 extends between opposing ends 82 and 84 of the pathway member 80. The distal end 82 of the pathway member 80 defines a terminal outer end 83. The pathway member 80 can include a hollow sleeve 81 fixed in the bore 86. The sleeve 81 can further can include a tip 85 protruding from the terminal outer end 83 of the pathway member 80 distally along the longitudinal direction L. The sleeve 81 and pathway member 80 can also be monolithic. The assembly body 51 can define a distal body 51b. The distal body 51b can further define opening 51c extending through the distal body 51b along a longitudinal direction L. The opening 51c is sized to receive at least a portion of the actuation member 53 and the pathway member 80. The base body 54b can also define an opening 54c. Thus, the distally disposed portion (near the distal end 82) of the pathway member 80 is slidably disposed within the actuation member 53, while the opposed proximal portion, for instance, the proximal end 84, is fixedly disposed within the base opening 54c so that the pathway member 80 cannot translate or move with relative to the base 54. The pathway member 80 is disposed in the actuator assembly 50 such that the proximal end 84 is axially aligned with the aperture 55 of base 54.

Figure 4:
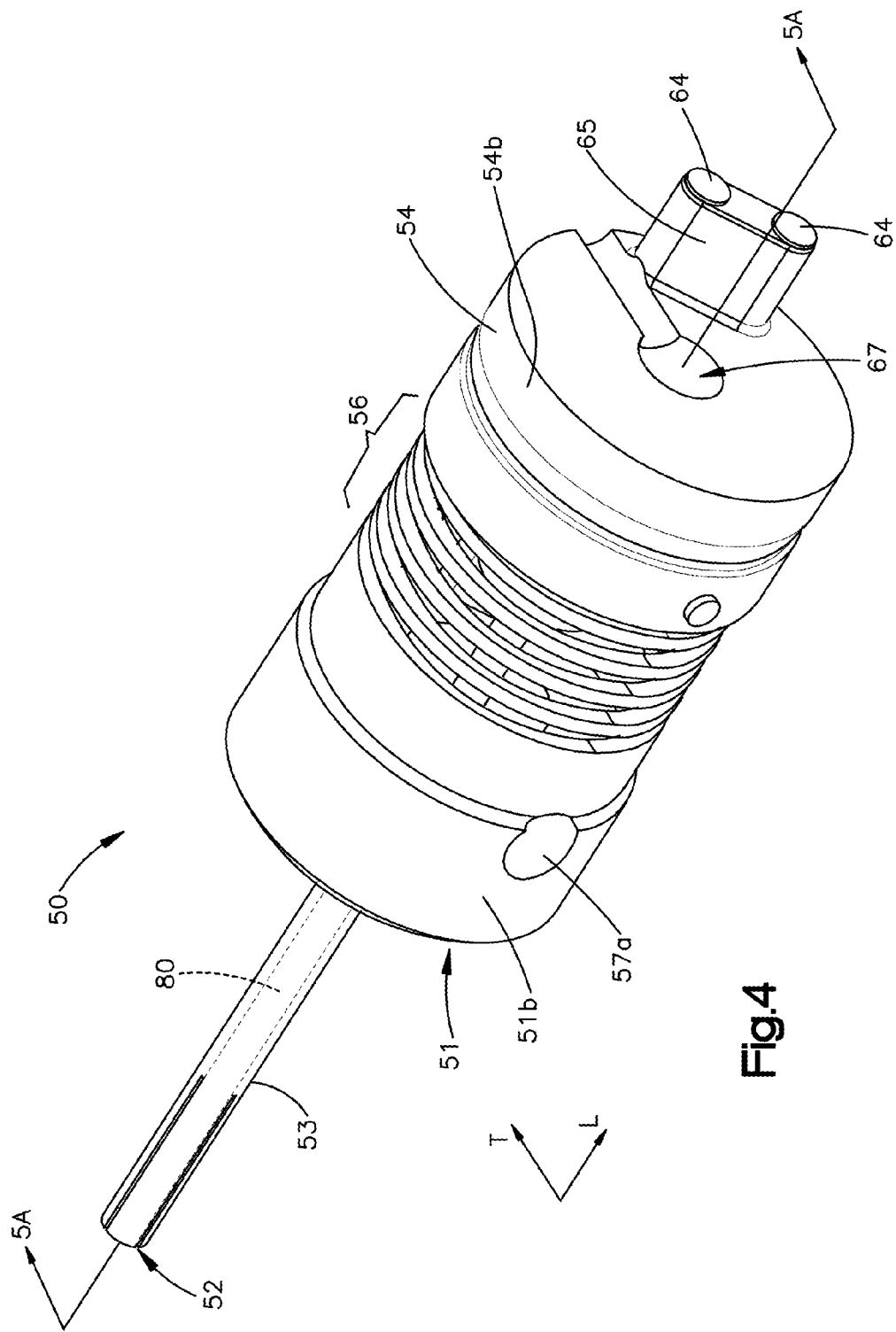
FIG. 4 is a perspective view of an actuator assembly used in the laser device shown in FIGS. 1A and 1B.

Continuing with FIGS. 4-5B, the actuator assembly 50 is configured so that when the fixation member 18 is received therein, the actuator assembly 50 can permit power to be supplied from the power source to the laser source 70. Thus, the actuator assembly 50 can complete an electrical connection between the laser source 70 and the power source 90 by moving from the first position configuration shown in FIG. 5A into the actuated position shown in FIG. 5B. In the illustrated embodiment, the first actuator assembly 50 includes at least one conducting member 60 configured to selectively connect or disconnect the power source 90 from the laser source 70. The assembly body 51 can define a recess 60c and the conducting member 60 can be partially disposed in the recess 60c such that the conducting member 60 extends proximally along the longitudinal direction L from the assembly body 51 toward the base 54. The conducting member 60 includes a conductive slat 62 extending proximally along the longitudinal direction L relative to the assembly body 51. The slat 62 is shown elongate along a direction transverse to the axis L (not shown). The slat 62 is conductive, and can be metallic, copper, gold, metallic blends or alloys thereof, or any other conducting material. The conducting member 64 and slat 62 can be an integral conductive body. The actuator assembly 50 can include an additional conducting member 64 carried by the base 54. The conducting member 64 is configured as a pair of conductive pins. The assembly base 54 includes a tab 65 extending proximally from relative to the base 54. The base body 54b can further define an opening 64c extending along the longitudinal direction L through the base 54b and the tab 65. A conducting pin pairs are disposed in the opening 64c. The slat 62 is sized to contact and bridge the distally oriented ends of conducting pin pairs 64 mounted in tab 65 of the base 54

The laser device body 12 can include one or more conducting members 74 supported by the laser device body 12 that are configured to contact the conducting members 60 and 64 of the actuator assembly 50. For instance, the conducting member 74 is disposed in the cartridge body 72 in electronic communication with the circuit 300. The base tab 65 is received by the cartridge slot 69 and the conductive pins pairs 64 form an electrical contact with the conducting member 74. The pin pairs 64 and conducting member 74 thus define a switch in the circuit 300. When the assembly 50 is in the first position as shown in FIG. 5A, a gap 63 extends between the conductive slat 62 and the conductive pin pair 64. As shown in FIG. 5B, when the actuation member 53 and assembly body 51 are displaced proximally in the longitudinal direction L the conductive pin pairs 64 contact the conductive slat 62 to form an electrical connection 63c. The connection 63c thus closes at least one or more of the switches in the circuit 300, which can permit power to be supplied to the laser source 70 to emit the laser beam.

Referring to FIGS. 4-6C, the actuation member 53 is configured to receive a fixation member 18 therein, which can permit the actuator assembly 50 to move from the first position to the actuated position. The actuation member 53 thus includes a fixation member receiving end 52 and an opposed end 53c spaced apart from the fixation member receiving end along the longitudinal direction L. The end 53c is received in the opening 51c of the assembly body 51. The actuation member 53 can define an inner tubular surface 66. The pathway member 80 is slidably disposed within the actuation member 53 along the surface 66. The actuation member 53 can be mounted, fused, threaded, and/or glued to the assembly body 51. Further, the actuation member 53 and assembly body 51 can be integrally formed.

The fixation member receiving end 52 is configured to at least partially receive the fixation member 18, such that the actuator assembly 50 is locked in the first position when the fixation member 18 is not received in the fixation member receiving end 52 of the actuation member 53. When the fixation member 18 is inserted in the receiving end 52, the first actuator assembly 50 is unlocked. Turning to FIG. 6A, the receiving end 52 of the actuation member 52 includes one or more flexible tabs 69 and at least one stop member 68 disposed on the tabs 69. The one or more flexible tabs 69 can flex when the fixation member 18 is received by the receiving end 52. The stop member 68 abuts the pathway member 80 such that slidable displacement the actuation member 53 along the pathway member 80 in the longitudinal direction L is prevented. For instance, the stop members 68 can extend inwardly along a transverse direction T from the tabs 69 to abut the terminal end 83 of the pathway member 80. The stop members 68 thus lock the actuator assembly 50 in the first position. The receiving end 52 further defines a circumferential groove 68a that is disposed along each tab 69 distal to the stop members 68, a terminal face 68c spaced from the groove 68a that is transverse the axis 1, and an inclined face 68b that extends between the groove 68a and terminal face 68c. When the fixation member 102 is positioned in the receiving end 52, the tabs 69 are deflected outwardly so that the stop members 68 are moved out of an abutting relationship with the pathway member 80. As shown in FIG. 6B, when the fixation member 18 is at least partially inserted into the distal end of the laser device 10, the stop member 68 no longer prevents the actuator 50 from the moving from the first position to the actuated position.

In alternative embodiments, any type of stop member 68 can be used to help prevent axial displacement of the actuation member 53 relative to the pathway member 80. For example, the stop member 68 can be a protrusion, tab, ridge, pin, detent, shoulder, tangs, wire, node or any structure or device that can be used to prevent movement of the actuation member 53 relative to the pathway member 80. In one exemplary embodiment, the stop members can for instance be tangs extending inwardly from the inner surface 66 and angled toward the longitudinal direction L. The tangs can abut the terminal end 83 of the pathway member 80, and can be deflected when the fixation member 18 is inserted in the actuation member 53 as described above. In yet another alternative embodiment for the stop member 68, the stop member 68 can be a curved member or ridge extending inwardly from the inner surface 66 of the actuation member 53 and abutting the pathway member 80. In another alternative embodiment, the fixation member receiving end 52 can be formed of a shape-memory polymer and is more ductile than the remainder of the actuation member 53, such that the fixation member receiving end 52 radially expands to receive the fixation member 18. The fixation member receiving end 52 is configured to slidably receive the fixation member 18 therein. For example, the fixation member receiving end 52 can have sloped surfaces 98 configured to allow easy fixation member 18 insertion into the actuation member 53. Further, the stop members 68 can be configured to have sloped or curved surfaces as needed to better receive and grasp the fixation member 18.

With reference to FIGS. 3A, 3B and 6A-6C, the laser device body 12 is configured to receive and insert the fixation member 18 into the target surgical site such that the actuation member 53 can be displaced into the actuated position. The fixation member 18 extends between a first end 102 and a second end 104 spaced from the first end along the fixation member axis 3. The first end 104 is referred to as the leading end and is inserted first into the cavity 4. The second end 102 is referred to as the trailing end and engages the receiving end 52 of the actuator assembly 50 as shown in FIGS. 6A-6C. The fixation member 18 includes a body 105. The trailing end 102 of the body 105 includes a head 113, a ridge 106 spaced distally from the head 113 along the axis 3, and a neck 107 that extends between the head 113 and ridge 106. The ridge 106 includes a proximal face 109 spaced from a distal face 108. The head defines a head or first cross-sectional dimension 102a, the neck defines a neck or second cross-sectional dimension 102b, and the ridge 106 defines a ridge or third cross-sectional dimension 102c. The head cross-sectional dimension 102a is the distance between opposing outer points (not shown) located on the head that lie on a plane that is perpendicular to the fixation member axis 3. Similarly, the cross-sectional dimension 102b of the neck 107 is the distance between opposing outer points located on the neck that lie on a plane that is perpendicular to the fixation member axis 3. Further, the cross-sectional dimension 102c of the ridge 106 is the distance between opposing outer points located on the ridge that lie on a plane that is perpendicular to the fixation member axis 3. In the illustrated embodiment, the ridge cross-sectional dimension 102c is greater than the head cross-sectional dimension 102*a*. Further, the neck cross-sectional dimension 102*b* is less than either or both of the head cross-sectional dimension 102*a* and the ridge cross-sectional dimension 102*c*. In an exemplary embodiment, the neck cross-sectional dimension 102*b* is less than both of the head cross-sectional dimension 102*a* and the ridge cross-sectional dimension 102*c*. The body 105 defines a proximal surface 111 that is transverse to the axis 3. Further, the fixation member body 105 defines a cannulation 114 that extends from the proximal surface 11 into the body 105 along the axis 3. A shaft 112 extends distally with respect to the head 113. As shown in FIG. 6B, when the fixation member 18 is received by the fixation member receiving end 52, the laser device body 12 can insert the fixation member 18 into the cavity 4 from an initial insertion position A1. In the position A1, the fixation member 18 is received by the actuation member 52 such that the fixation member head 113 is disposed in the groove 68*a* and the fixation member ridge 106 is positioned to abut the bone surface 6 surrounding the cavity 4. The fixation member ridge 106 can serve as a stop that abuts the terminal face 68*c* of the actuation member 53. As shown in FIG. 6C, when the user urges the laser device 10 and the fixation member ridge 106 upon the target surgical site surface 6 to the inserted position A2, the bone surface 6 applies an opposing force F (not shown) that displaces the actuation member 53 proximally along the longitudinal direction L relative to the pathway member 80. Proximal displacement causes the cannulation 114 to receive the tip 85 of the pathway member 80. Further, because the stop members 68 are deflected outwardly, the actuation member 53 and also the assembly body 51 can be displaced in a longitudinal direction L, which also displaces the assembly body 51 so as to permit activation of the laser device 10. Displacing the actuation member 53 completes the electrical connection 63*c* among conducing member 60, 64 and 74, as discussed above. Further, with the fixation element ridge 106 abutting the terminal face 68*c* of the receiving end 52 of the actuation member 53, the fixation member 18 substantially closes the distal end 12 of the laser device 10 to minimize any stray laser beam or diffused light that is not guided into fixation member 18 or absorbed by the fixation member 18.

Referring to FIGS. 1A through 2B the second actuator 30 can be supported by the laser device body 12. The second actuator 30 is configured to open and closes a switch that electrically connects the power source 90 and laser source 70. When the second actuator 30 is in the first position (FIG. 1A) that switch is open and the power source 90 is disconnected from the laser source 70. When the second actuator 30 is in the actuated position (FIG. 1B) the switch is closed the power source 90 is electrically connected to the laser source 70. The second actuator 30 opens or closes the switch by using detection elements carried by the second actuator member. The detection elements can be magnets. When second actuator is moved so that the magnets are closer to laser device body, the magnet(s) closes the electronic switch. When the second actuator is moved away from the laser device body, movement of the magnet(s) away from the laser device body causes the switch to open. The magnet can emit a magnetic field, such that movement of the second actuator 30 from the first position to the actuated position brings the magnetic field closer to the switch to either close the switch when a portion of the magnetic field is within a predetermined distance of the switch, or open the switch when the portion of the magnetic field is outside of the predetermined distance. The predetermined distance can be selected by the based on the magnet and proximity of the switch to the actuator when the actuator is in the second actuation position.

In the illustrated embodiment, the second actuator 30 can include a free end 32 opposed to a pivot connection 34 located near the laser device body 12, and one or more projections 38 and 39 (one, two or more members can be used) protruding from the second actuator 30 that are configured to engage the laser device body 12. The projections 38 can carry the detection element(s). The second actuator 30 can include engagement tabs 35 (FIG. 2B) that connects the second actuator assembly 30 to the laser device body 12, although any connection type can be used. The pivot connection 34 may bias the second actuator assembly 30 in the first position. Thus, a user can deflect the second actuator assembly 30 toward the laser device body 12 into the actuated position. The laser device body 12 defines one or more openings 38*a* and 39*a* that are sized to receive the one or more projections 38 of the second actuator 30. Thus, movement of the second actuator 30 from the first position to the actuated position moves the projections 38, and the magnets carried by the projections 38, closer to the switch which closes the switch. In another embodiment, when the second actuator 30 is in the actuated position the magnetic field causes the switch to close permitting the power source 90 to supply power to the laser source 70.

The second actuator 30 can include a pin 36 that extends from the free end 32 of the actuator 30. The assembly body 51 can define transversely directed bore 57*a* that is sized to receive therein the pin 36. When the first actuator assembly 50 is in the actuated position, bores 37*a* and 57*a* are axially aligned. When the second actuator assembly 30 is pressed toward the device body 12 the pin 36 is inserted in the aligned housing bores 37*a* and the bore 57*a*. The pin 36 held by the bores 37*a*, 57*a* provides a tactile indication to the user that the actuator assembly is in the actuated position. For instance, when the bores are not aligned, the pin 36 may not be received fully in the bores 37*a*, 57*a*.

The second actuator assembly 30 is shown as a lever. It should be appreciated that alternative embodiments of the second actuator assembly can be used for the same purposes as described herein. Accordingly, the second actuator assembly can be any device used to selectively cause a switch in an electric circuit to open, close, or alternate between an opened and closed positions. For example, the second actuator assembly can be a button, that when depressed, closes a switch in a circuit. In another embodiment, the second actuator assembly can be a toggle moveable to cause the switch to open and close. Other embodiments include a slide mechanism that can be slid into a position by the user to cause a switch in an electric circuit to close.

Figure 8:
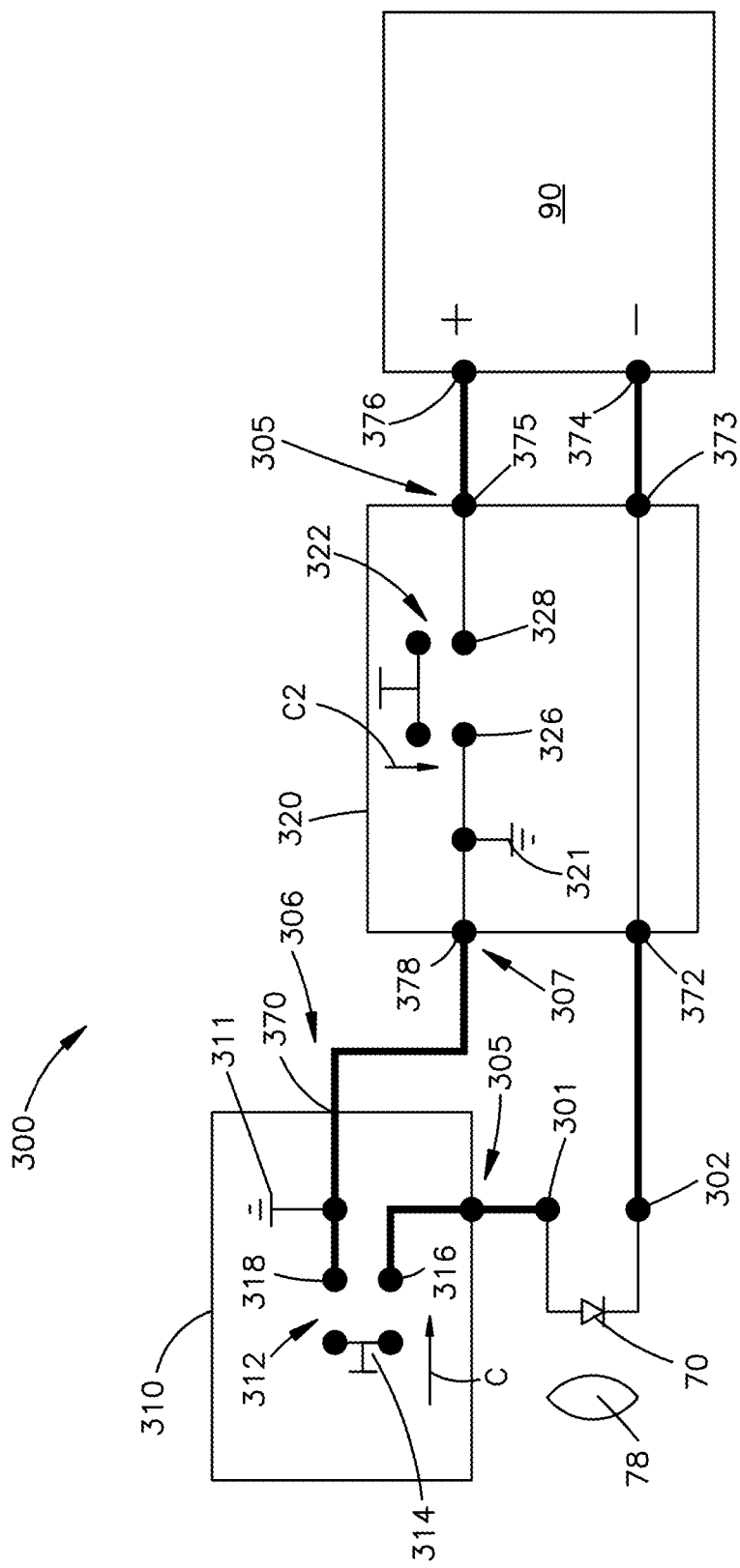
FIG. 8 is a schematic of a circuit used to supply power to a laser source in the laser device shown in FIG. 1.

Turning next to FIG. 8, an electronic circuit for selectively permitting power to be supplied the laser source 70 is configured to be installed in a laser device of the type that includes an actuation member 53, a power source 90, and a laser source 70. The circuit 300 can include an electrical conductor having first and second ends 301 and 302 that are configured to be placed in electrical communication with the laser source 70 and the power source 90. The circuit 300 can include a first switch assembly 310 disposed between first and second portions 305 and 306 of the electrical conductor at a location between the first and second ends 301 and 302. A second switch assembly 320 can disposed between first and second portions 307 and 308 of the electrical conductor at a location between the first and second ends 301 and 302. The first and second switch assemblies 310 and 320 are in electrical communication with the laser source 70 and power source 90. When the electrical circuit 300 is installed in the laser device 10 and the first and second switches assemblies 310 and 320 are in their respective closed positions, the first and second ends 301 and 302 are placed in electrical communication with each other so as to cause power to travel along the electrical conductor from the power source 90 to the laser source 70. The first and second switches assemblies 310 and 320 can be directly attached to terminals of the laser and power source, or can be connected via another electrical conductor.

The first switch assembly 310 includes the first switch 312 comprising a moveable contact 314, and first and second contacts 316 and 318, and appropriate grounds 311 as needed. The first switch 312 is responsive to a first input so as to alternate between a normally open position and a closed position. When the first switch 312 is in the open position, the first and second portions 305, 306 are electrically isolated from each other. When the first switch 312 is in the closed position, the first and second portions are placed in electrical communication with each other. For instance, the moveable contact 314 can move in response to a mechanical effort or response, such as when the connection is formed by the actuator assembly 50 in the actuated configuration described above (see FIGS. 5B and 7B). The first contact 316 is operably connected to the laser source 70. The second contact 318 includes a terminal 370, which is connectable to an additional terminal 378 on the second switch assembly 320. The first switch 312 can be opened as shown in FIG. 8, or closed in response to the positions of the actuators 30 or 50. When the first switch 312 is closed, electrical current can flow through the first switch assembly to the laser source 70.

The second switch assembly 320 is disposed between third and fourth portions of the electrical conductor at a location between the first and second ends 301 and 302. The second switch assembly 320 includes the second switch 322 comprising a moveable contact 324 and first and second contacts 326 and 328, and an appropriate ground 321 as needed. The second switch 322 is responsive to a second input that is different from the first input to alternate between a normally open position and a closed position. For instance, the moveable contact 324 is operable to close the switch 322 in response to an input. The first contact 326 is operably connected to the power source 90 via one or more terminals 375 and 376. The second contact 326 is operably connected to the terminal 378, which is connectable to the terminal 370 on the second switch assembly 320. The power source 90 is operably connectable to the laser source 70 through the terminals 372 and 373. The second switch 322 can be opened as shown in FIG. 8, or closed in response to input. The input can be movement of the second actuator 30 from the first position into the actuated position, receipt of a signal from a sensor, or the presence of the magnet in proximity to the switch assembly 320. When a magnet carried by the second actuator 30 is moved so that the magnet is within the vicinity of the switch assembly 310, the contact 324 moves to the closed position. Thus, the circuit 300 is operable to supply current from the power source 90 to the laser source 70 when the first switch assembly 310 is in a closed position and the second switch assembly 320 is a closed position. The first switch assembly 310 and a second switch assembly 320 can alternate between the open and closed positions in response to any particular input. Thus, the first input can close the first switch 312 and the second input can close the second switch 322, and vice versa.

Referring to FIGS. 2D and 8, it should be appreciated that the laser source 70 can be any device, mechanism, component, collection of components, or system that can emit a laser beam. As with typical laser sources, the laser source 70 can include an active medium, a high reflectance mirror, and a partially transmissive mirror (output mirror), and an excitation mechanism, or power source as used herein, that is used to energize the active medium. The phrase "power source" as used herein means the power source used to energize the active medium of the laser. The mechanism of laser formation is well known and will not be detailed herein. However, it should be understood that any suitable laser source could be used. Accordingly, multiple laser types can be used, such as a wavelength, continuous wave, or pulsed lasers.

The laser source 70 can be targeted to the particular treatment needs, and its delivered wavelength or power output varied. In one embodiment, the laser source 70 can be configured to emit light in range from 400 nm to 1600 nm. For instance, the laser source 70 can be configured to emit light at 670 nm or 808 nm. In addition, the laser source 70 can be configured for a power output between about 0.1 W to about 10.0 W. The power can be depend on the size of the fixation member 18. For example, for fixation members with a shaft diameter of 1.6 mm and a length of 6 mm (the length is defined between ends 102 and 104 of the fixation member 18), the power output can range between about 1.1 W to about 1.5 W, preferably about 1.2 W. For fixation members with a shaft diameter of 3 mm and a length of 12 mm, the power output can range between about 6 W to about 8 W, preferably about 7 W. Further, the laser source 70 is configured in an embodiment as a class 2, 3 or 4 laser. IEC 60825-1 classifies lasers as Class 1, 2, 3 or 4 lasers using the concept of accessible emission limits (AEL). The AEL can be a maximum power (in W) or energy (in J) that can be emitted in a specified wavelength range and exposure time that passes through a specified aperture stop at a specified distance, which is further defined in Standard IEC 60825-1. "AEL" as used in this document means the same thing as the "AEL" set forth in IEC 60825-1. Laser sources that emit continuous laser beam having AELs in the wavelength range from 315 nm to far infrared that is greater than at least 0.5 W are considered Class 4 lasers and such laser sources can be used with laser device as described herein. Laser sources that emit pulsed lasers between 400 and 700 nm with at least 30 mW AEL or higher are Class 4 lasers, and such laser sources can be used with the laser device as described herein. It should be appreciated that the laser source 70 does not have to be a Class 4 laser. In alternate embodiments, the laser source 70 can be any of a Class 1, 2, 3 or 4 laser.

The fixation member 18 and laser device 10 are configured to prevent the laser beam from emanating from the laser source 70 and laser device 10 during the active configuration. When the fixation member 18 is disposed in the actuation member 53, and the pathway member tip 85 is disposed on the fixation member cannulation 114, the laser beam is enclosed such that laser beam is not visible to a user or persons near the laser device. In an active configuration, the laser device 10 and fixation member 18 block the laser beam from being emitted from the laser device 10 while the fixation member can substantially absorb laser beam emitting from the laser source 70. This reduces the risk of tissue and/or eye damage associated with using high-powered lasers, e.g. class 3 or 4 lasers. Further, the fixation member 18 is configured to receive energy from a Class-2, -3, or -4 laser beam, and in response to the received energy, soften the fixation member at the target surgical location. The fixation member 18 is configured to absorb a sufficient quantity of the received energy to emit no more than the energy that a Class 1 laser beam emits. Stated differently, a laser source 70 can be classified as a Class 2, 3 or 4 laser, but when used in a laser device 10 as described herein, the laser device 10 is classified as a Class 1 laser device 10 according to IEC 60825-1. The fixation member 18 is configured to engage the laser device 10 and partially absorb the laser emitting from the laser source 70. The portion of the laser not absorbed by the fixation member 18 may be diffused by the fixation member 18. Thus, when the laser device 10 is in the active configuration and the laser beam is emitted from the laser source 70, the fixation member 18 and laser device 10 substantially prevent any external visual observation of the laser by the user or other person in close proximity to the laser device, e.g., the surgeon or other operating room staff.

Turning now to FIGS. 3A-3D, an exemplary fixation member 18 includes a body 105 that is formed of a polymeric material. As discussed above, the body 105 extends between the insertion end 104 and the spaced apart trailing end 102. The fixation member cannulation 114 receives therein the tip 85 of the pathway member 80 (FIG. 6C) when the actuator 50 is in the actuated position as discussed above. Such a configuration permits the laser beam emitted from the laser source 70 to enter the fixation member body 105 through the cannulation 114. Any absorbent agents can then absorb a substantial amount of the laser. Further, the ridge 106 abuts the terminal face 68c of the actuation member 53 to substantially close the distal end 112 of the laser device 10. Any light diffused by the fixation member 18 that does emanate from the fixation member 18 is not harmful to users, observers, and/or the patient. In alternative embodiments, the fixation member 18 can have other configurations. For example, the fixation member can have a conical or frusto-conical shape, such that the trailing end 102 has a cross-sectional diameter that is larger than the cross-sectional diameter for the leading end 104. In other embodiment, the fixation member 18 can have a generally cylindrical shape.

Figures 3A, 3B:
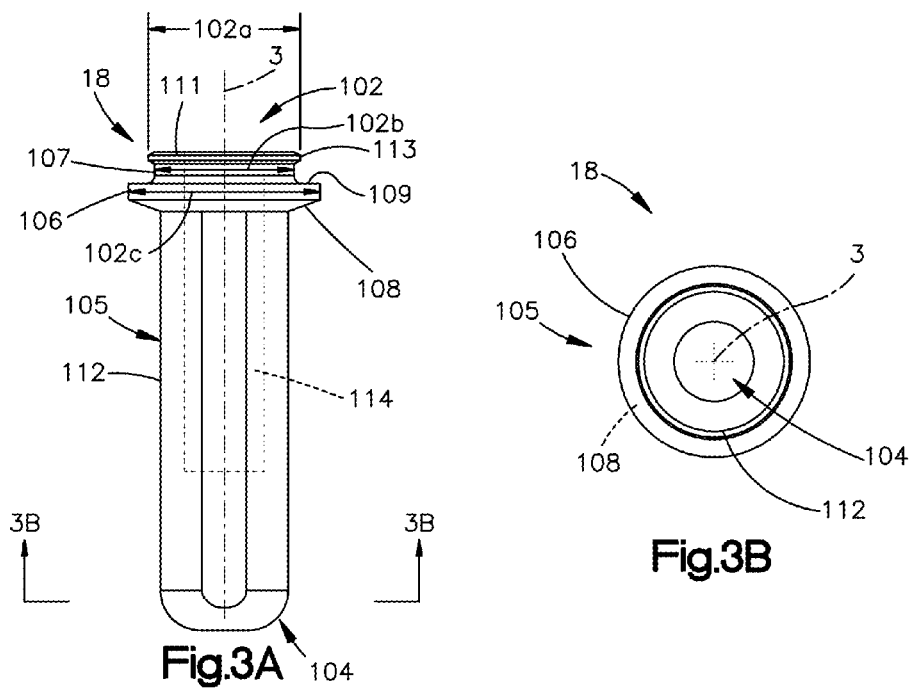
FIGS. 3A and 3B are side and end views, respectively, of a fixation member used with the laser device shown in FIGS. 1A and 1B.
Figures 3C, 3D:
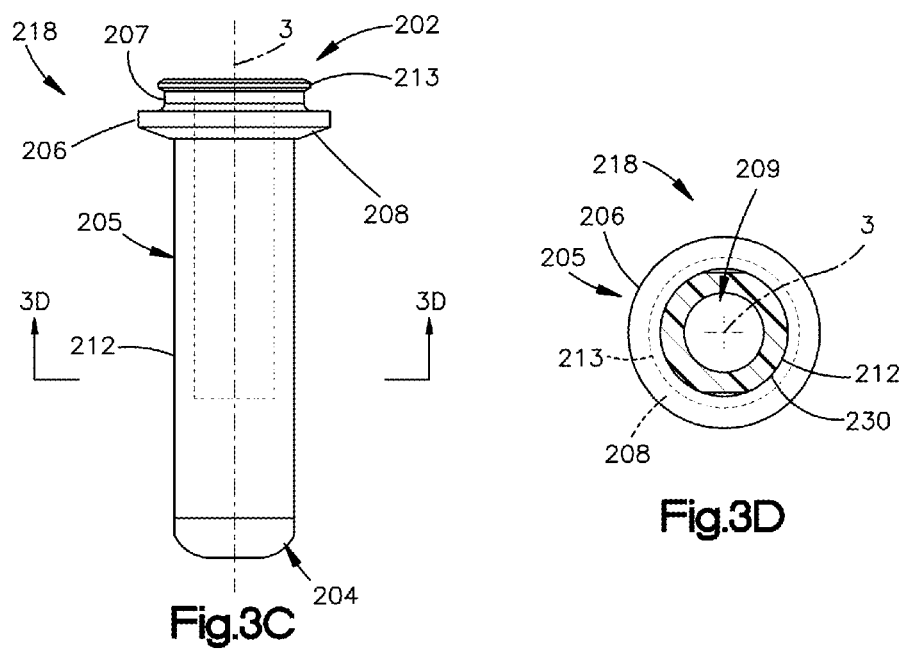
FIG. 3C is a side view of another embodiment of a fixation member used with the laser device shown in FIGS. 1A and 1B.
FIG. 3D is a section of the fixation member shown in FIG. 3C taken along lines 3D-3D shown in FIG. 3C.

Laser absorption is the result of polymeric body composition, additional polymeric components, and/or agents selected to aid in laser absorption. Polymers used to form the fixation member 18 can be in suitable biocompatible polymer, such as polyetheretherketone (PEEK), polyetherketoneketone (PEKK), polylactic acid (PLA), polyglocolic acid (PGA), Polyglycolic-Lactic Acid (PGLA), polymethyl methacrylate (PMMA), polycaprolactone (PCL) and others. It should be appreciated that any polymeric formulation suitable for medical uses and capable of softening or liquefaction can used to form the fixation member 18. The composition of the polymeric body is selected to aid in laser absorption. Specifically, the composition of the polymeric body can include between about 0.1% and about 2% by weight of an agent that aids in laser absorption. Preferably, the agent is about 0.75% by weight of the composition. The agent can an additive that is regulatory compliant for medical use, for example, such as U.S. Federal Drug Administration (FDA) classified D&C Blue No. 6. The agent can be added in the form of a coating disposed on the outer surface of the fixation member 18. FIGS. 3C and 3D illustrate an additional embodiment of the fixation member 18 having thereon an absorptive coating 220 covering the fixation member body 205. Alternatively, the agent can be blended within the polymer melt when the fixation member 18 is formed. In other alternative embodiments, the fixation member 18 can be a formed a bi-component polymeric body. Such a bi-component polymer body can comprise a first component and a second component, wherein a second component is disposed within the first component, and wherein the first component is capable of at least substantially absorbing the laser. Each of the first and second components as described herein can be manufactured as described above. That is, either or both the first and second components can include any one, or a combination of the agents as described above.

It should be appreciated that the fixation member 18 can be an anchor, rivet, pin, screw, or any device or structure used to couple or fix an implant to tissue. In other embodiments, the fixation member 18 can also include additional fixation member components that aid in fixation. One such alternative embodiment is a fixation member 18 and suture structure. The fixation member 18 is formed so that a suture extends through a bore disposed in the polymeric body 104 orthogonal to the fixation member axis A. The suture can also extend across the leading end of the fixation member 18, disposed in channel formed to receive the suture. Free opposed ends of the suture extend from and along the sides of the fixation member 18 past the trailing end 102 of the fixation member 18. When such a fixation member 18 is inserted into the cavity formed in a plate, for example. The laser device 10 can be activated to melt the fixation member 18 as described herein. The free ends of the suture can be pulled, forcing the softened fixation member 18 to morph into a rivet. Other exemplary fixation members 18 and fixation member systems suitable for use in the present invention are described in WO 2009/036576, WO 2012/003294, and WO 2012/087426, the disclosures of which is incorporated by reference in their entirety.

Figure 7A:
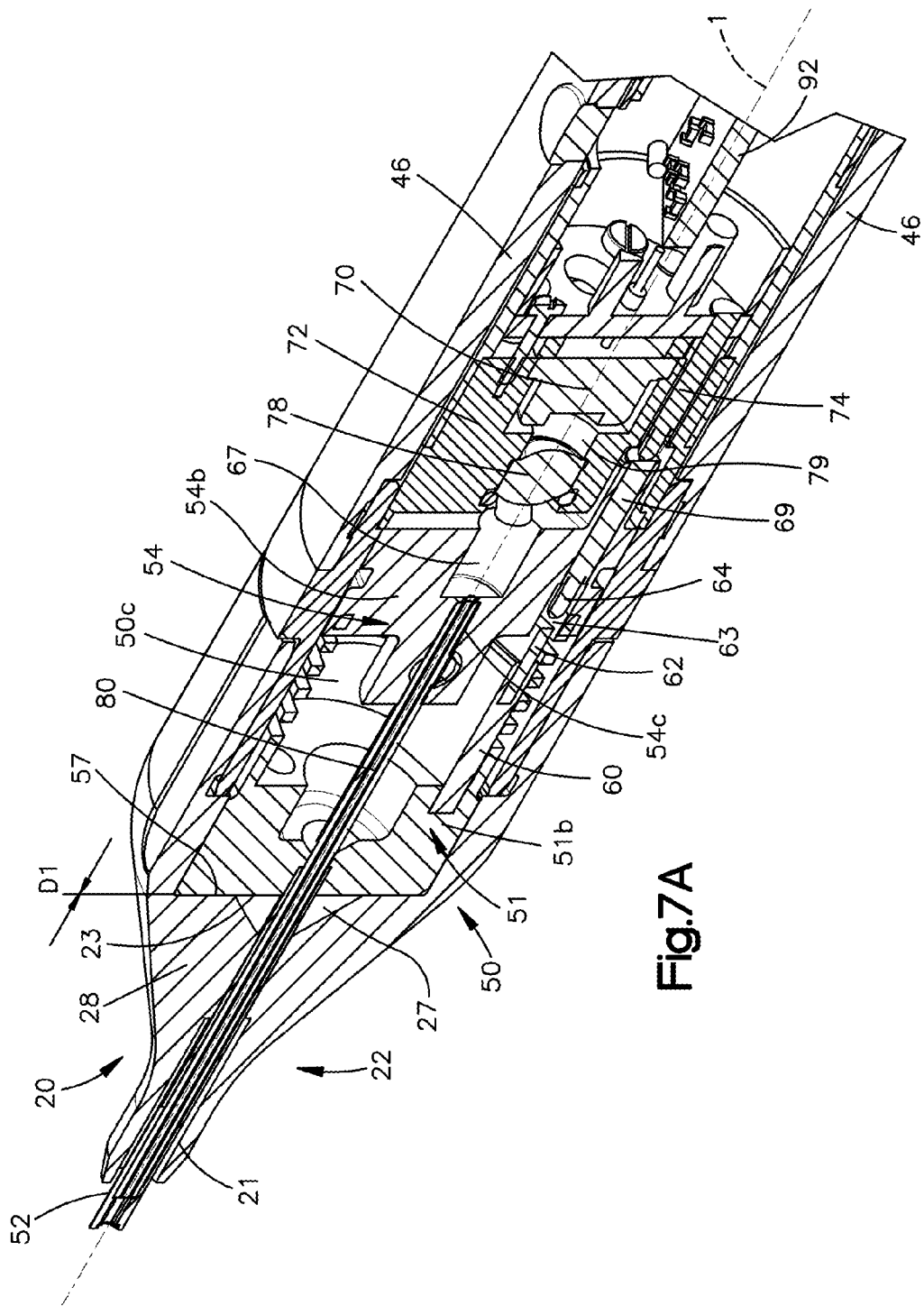
FIG. 7A is a perspective cross-sectional view of the laser device shown in FIG. 2B, illustrating the actuator assembly in a first position and the laser device in the inactive configuration.
Figure 7B:
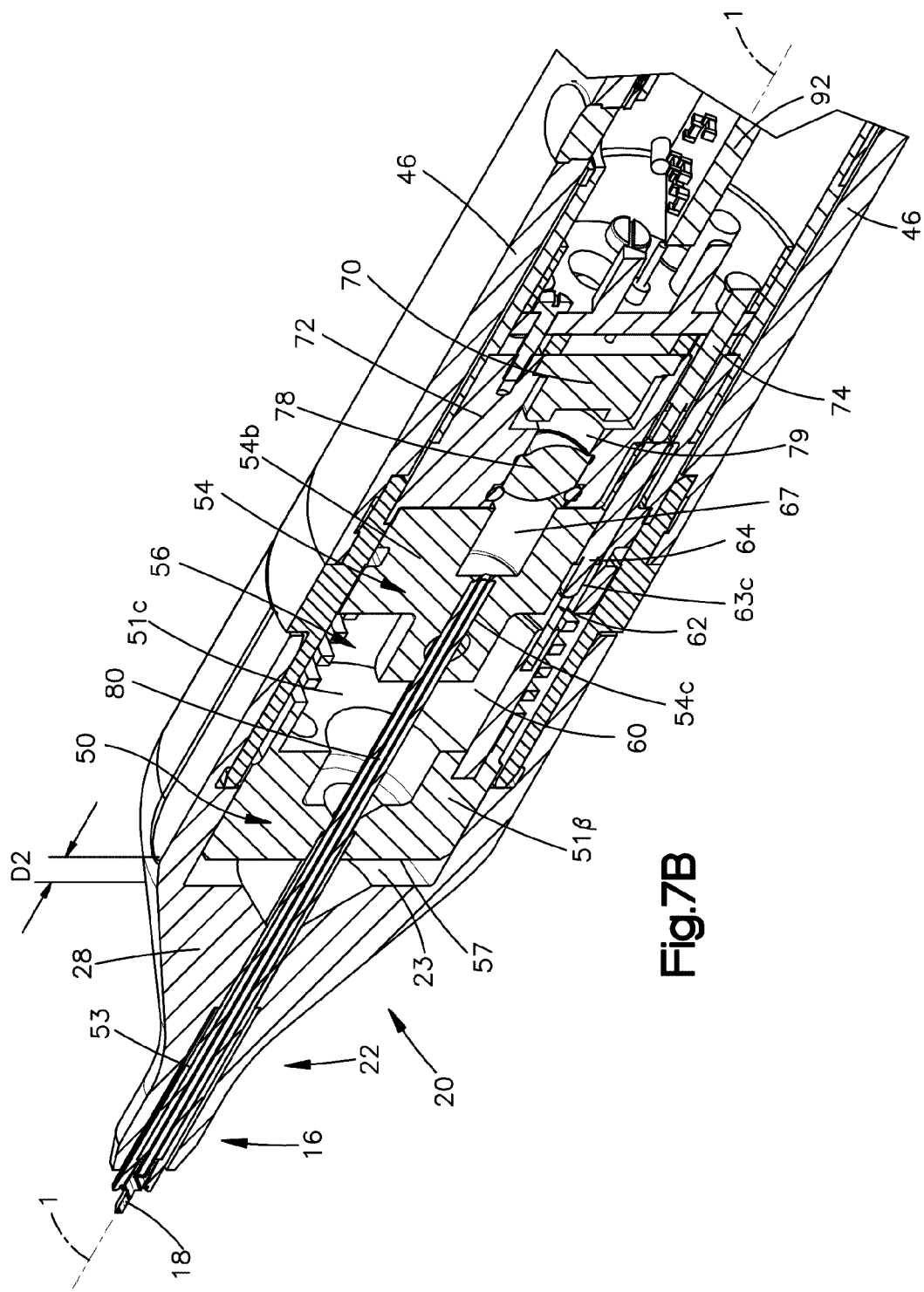
FIG. 7B is a perspective cross-sectional view of laser device section shown in FIG. 2C, illustrating the actuator assembly in an actuated position and the laser device in the active configuration.

Referring to FIGS. 7A and 7B, the first and second actuator assemblies 30 and 50 are configured to switch the laser device between the active configuration and the inactive configuration. The actuator assembly 50 can include an actuator assembly surface 57 that can be defined by a distal-most surface of the assembly body 51. The laser device body 12 can define a device body inner surface 23 that faces the assembly surface 57. In the inactive configuration shown in FIG. 7A, the distance between the assembly surface 57 and the inner surface 23 is defined as first distance D1. When the actuator assembly 50 is in a first position, the first distance D1 can be equal to about zero, or can be greater than zero. When the actuator assembly 50 is proximally displaced relative to the device body 12 along the longitudinal direction L as described herein, the assembly surface 57 is spaced from the device inner surface 23 along the longitudinal direction L a second distance D2 that is greater than the first distance D1. Further, the distance D1 is about the distance required to maintain the gap 63 between the slat 62 and the pin pairs 64 as described above. As shown in FIG. 7B, when the fixation member 18 is inserted into the actuation member 53, and the force F is applied to the fixation member 18, the fixation member receiving end 52 displaces the actuator assembly 50 into the actuated position. The force F is applied by user pressing the device and fixation member against bone surface 6. The actuation member 53 and assembly body 51 are displaced along the longitudinal axis L the distance D2 so that the slat 62 comes into contact 63c with the conductive pin pairs 64. Contact between slat 62 and conductive pins 64 closes a switch 312 on circuit 300 to partially close the electrical connection between the laser source 70 and the power source 90. Further, the second actuator assembly 30 is also moved to the actuated position (as shown in FIG. 1B) such that the projections 38, 39 engage the openings 38a, 39b. The magnets in the second actuator 30 cause an second switch 322 to close, thereby completing the electrical connection between the laser source 70 and the power source 90. With the electrical connection complete, the power is supplied to the laser source 70 and an laser beam is emitted into the fixation member 18, which then softens or melts the fixation member 18. During laser beam emission, the fixation member 18 then at least partially absorbs the laser beam and diffuses the remaining laser light. Because the fixation member 18 is positioned on the distal end 16 of the laser device 10, laser operation or emission is enclosed shielding a user from any harmful light emanating from the surgical site during the procedure.

Figure 9A:
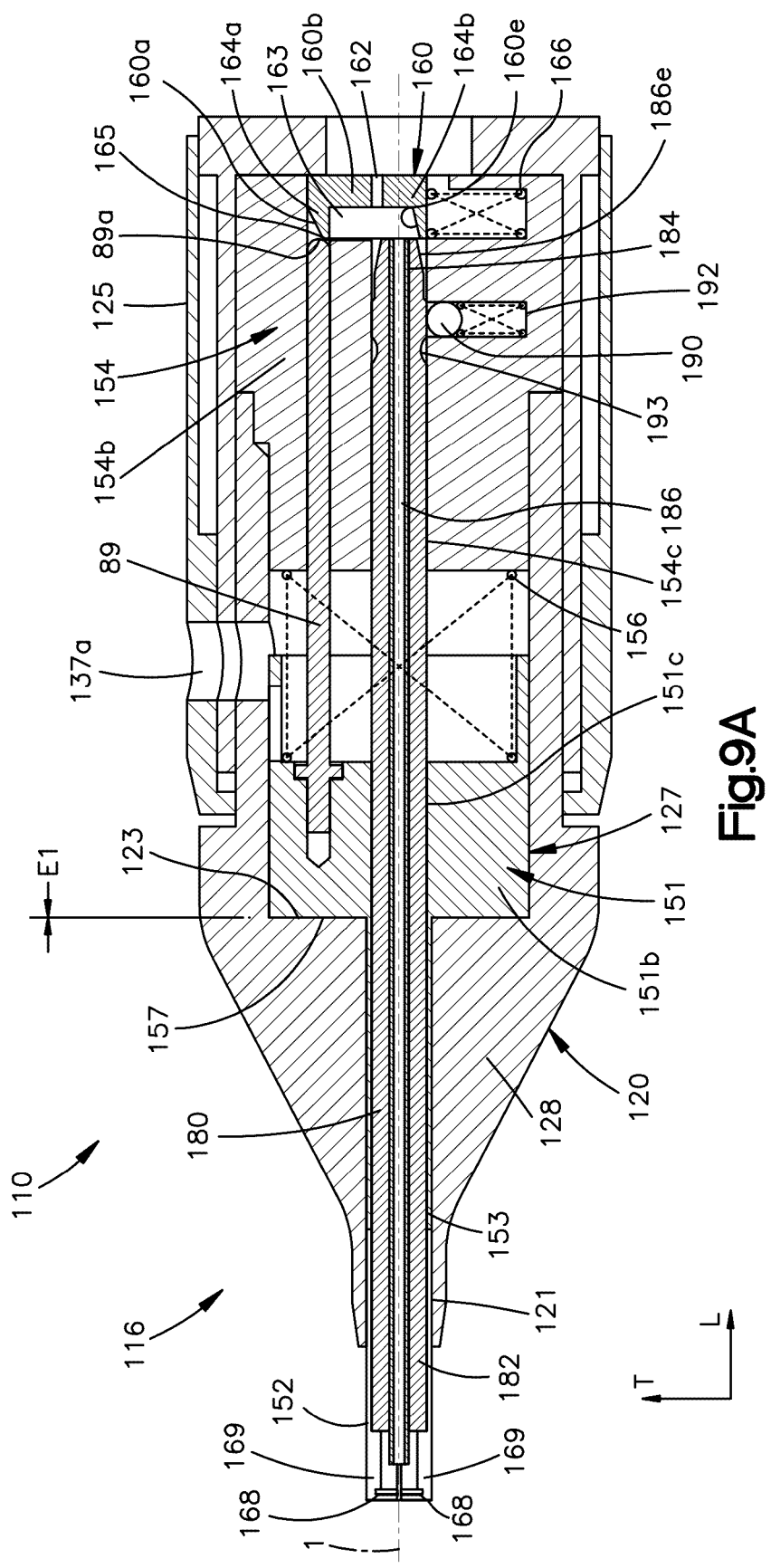
FIGS. 9A, 9B and 9C are partial cross-sectional views of a laser device according to another embodiment of the invention that illustrates how the laser device can be manipulated from an inactive configuration shown in FIG. 9A to an active configuration shown in FIG. 9C, respectively.
Figure 9B:
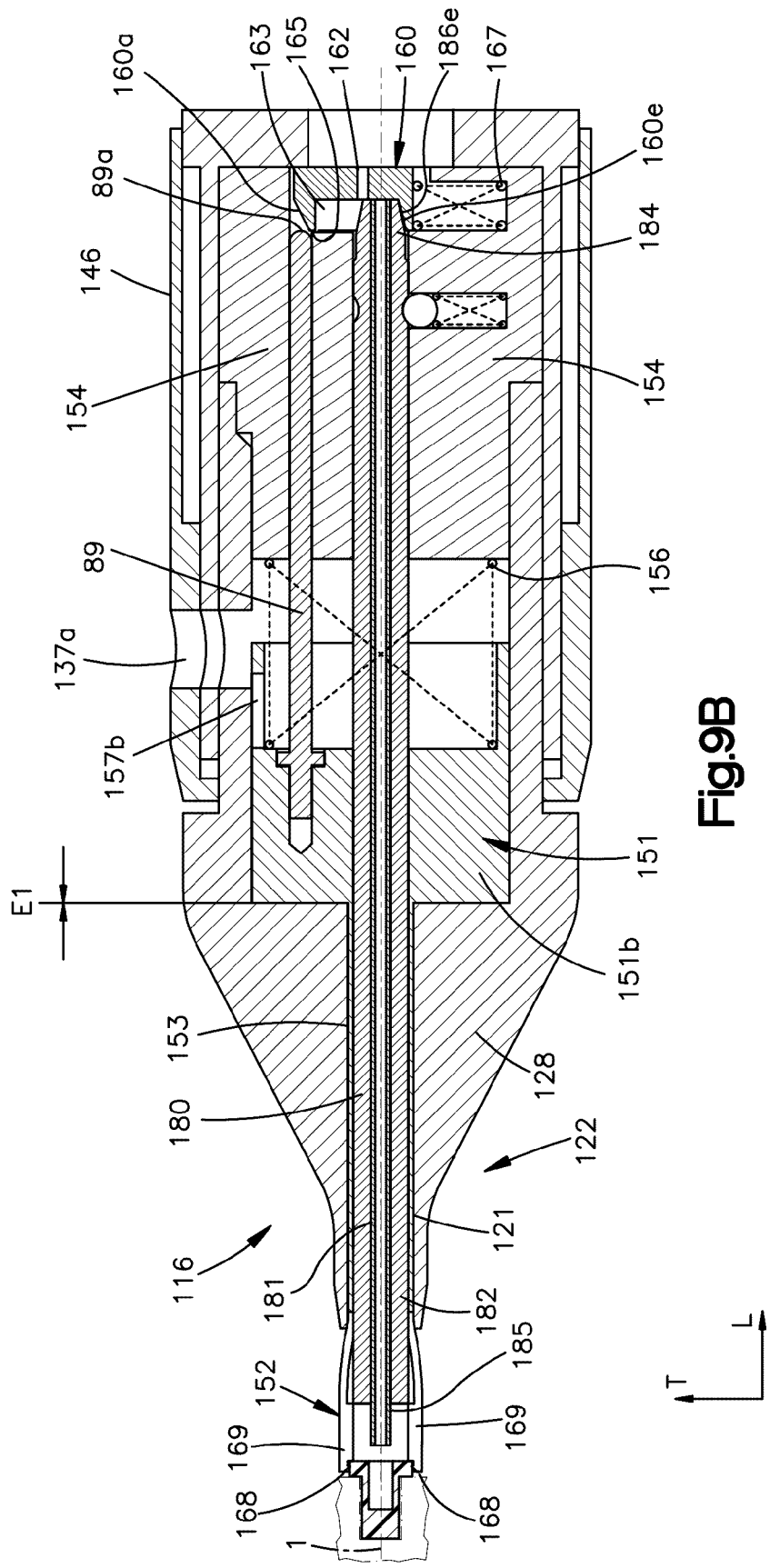
Figure 9C:
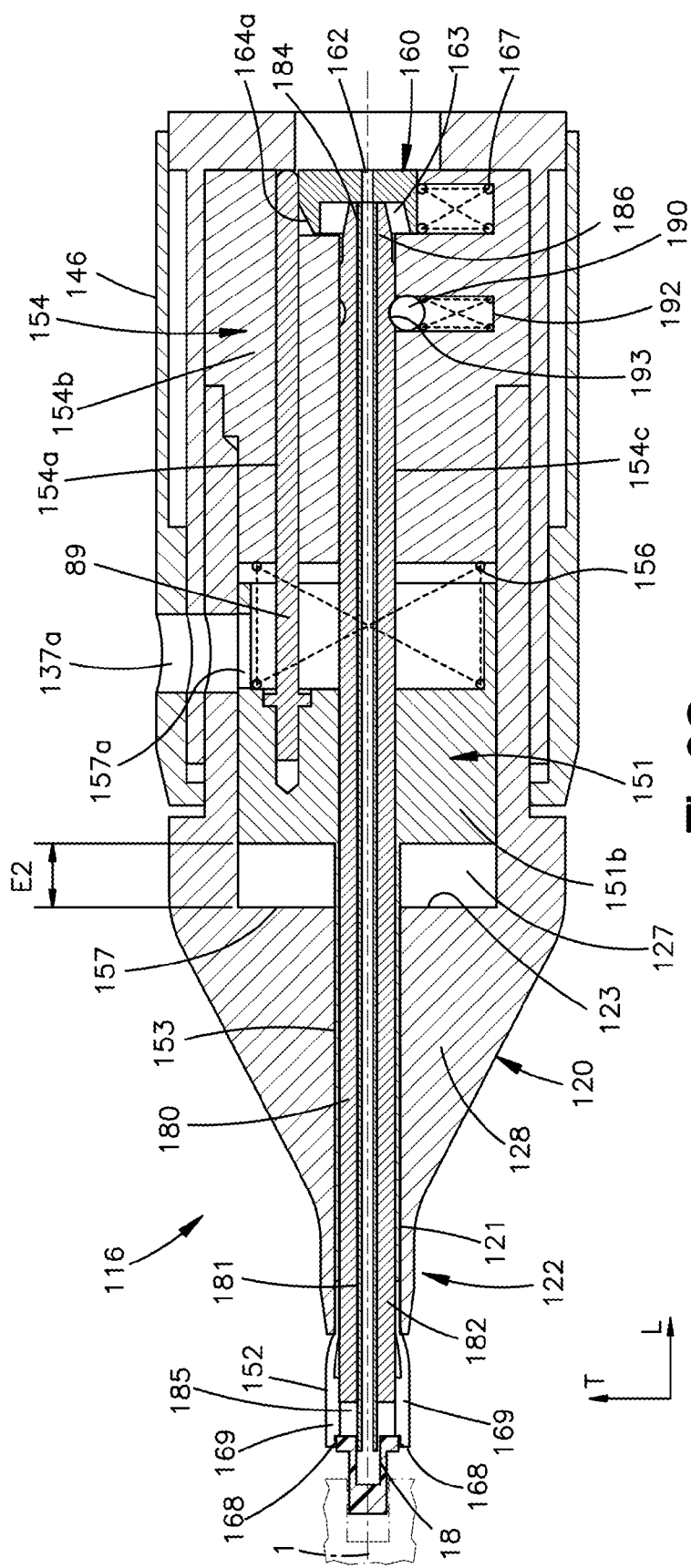
Figure 10A:
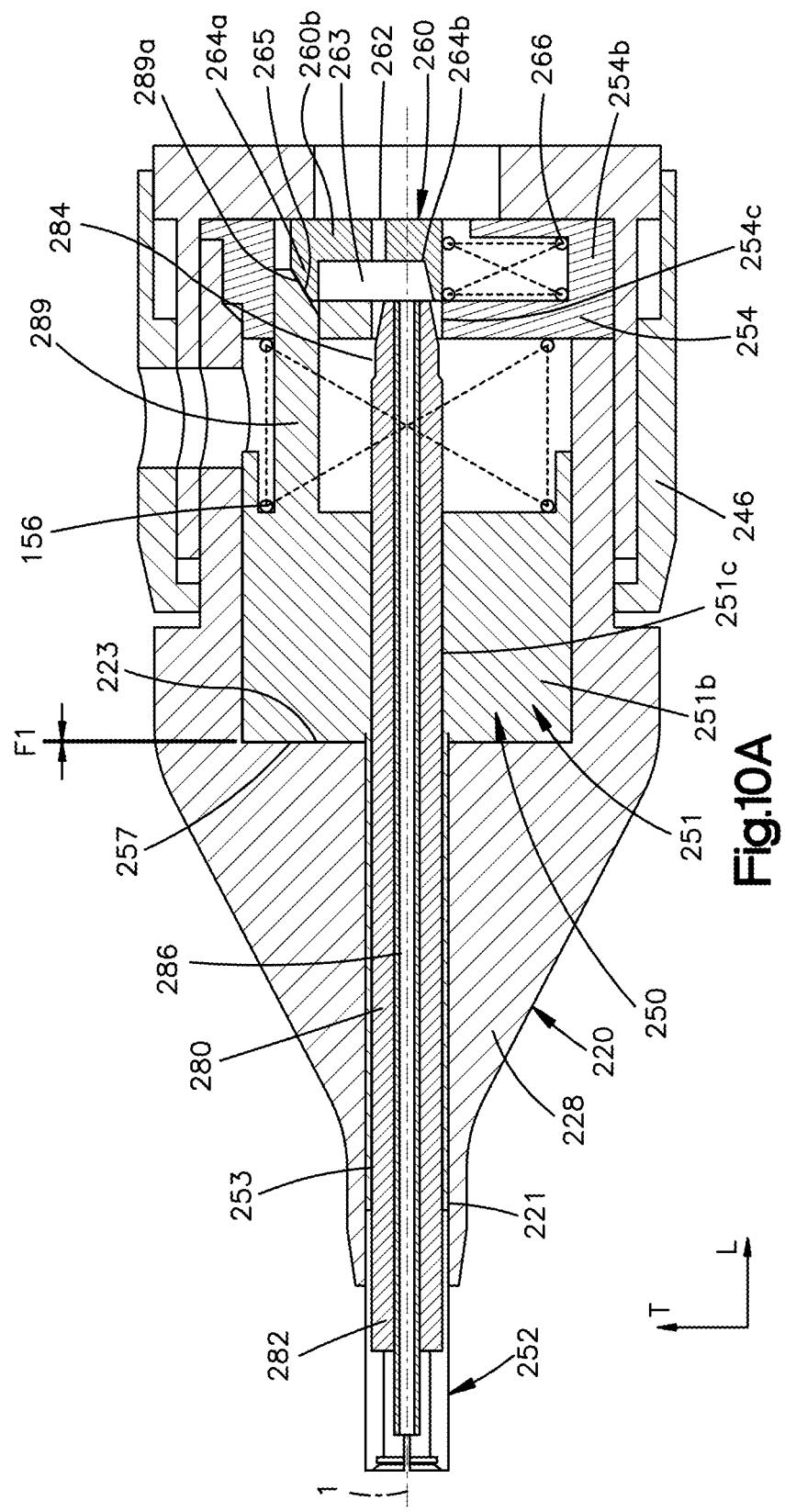
FIGS. 10A and 10B are partial cross-sectional views of a laser device according to another embodiment of the invention, illustrating the laser device in an inactive configuration and an active configuration, respectively.
Figure 10B:
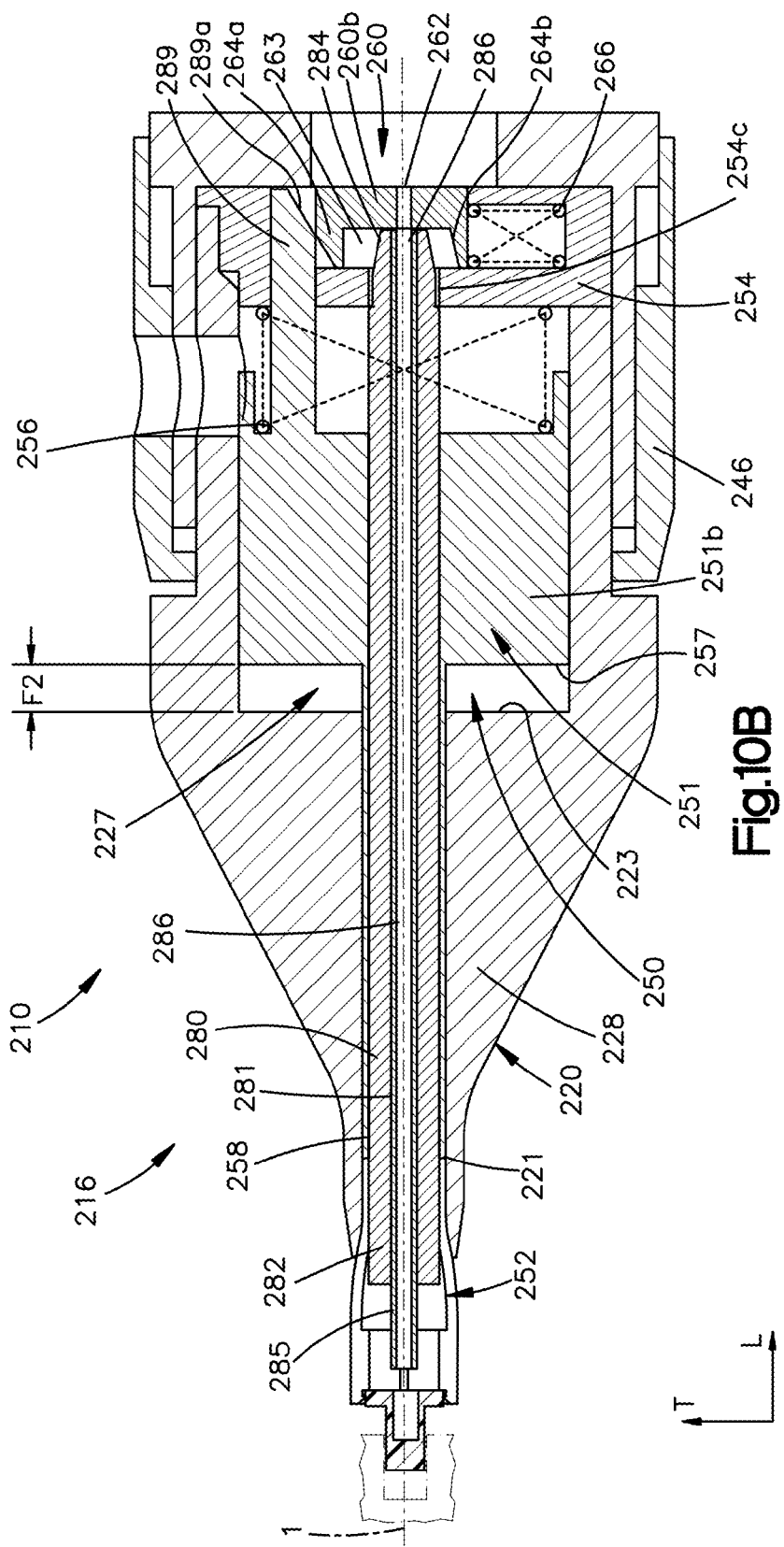

Referring to FIGS. 9A-10B, in accordance with an alternative embodiment, the laser device 10 can include a shutter assembly 160 or 260 that is configured to selectively place the laser source in operative alignment with the distal end, and thus in operative alignment with the fixation member when the fixation member is received by the distal end of the laser device 10. FIGS. 9A-9C illustrate an embodiment of the shutter assembly configured to move in two phases between a closed configuration (FIGS. 9A, 9B) and an open configuration (FIG. 9C). FIGS. 10A and 10B illustrates an embodiment of the shutter assembly 260 configured to move in a single phase between a closed configuration (FIG. 10A) and an open configuration (FIG. 10B).

Referring first to FIGS. 9A-B, in accordance with an alternative embodiment, the laser device 110 can include a laser device body 112 having a distal end 116, and a proximal end 114 spaced apart from a distal end 116. The device body 112 can further define a device housing 120 configured to support at least one actuator assembly, similar to the embodiment described above. Further, the laser device 110 also includes a laser 70, power source 90, and at least one circuit 300, which are similar to the embodiment described above and shown in FIGS. 1A-8. In accordance with an alternate embodiment, the laser device 110 includes an actuator assembly 150 and a pathway member 180 that are operably coupled with the shutter assembly 160 configured for two phases operation. The shutter assembly 160 is configured to move in a first phase from a locked position (FIG. 9A) to an unlocked position (FIG. 9B), and then in a second phase from a closed configuration (FIGS. 9A, 9B) into an open configuration (FIG. 9C). The locked position (FIG. 9A) is when the actuator assembly 150 is locked in position by the shutter assembly 160, and the unlocked position (FIG. 9B) is when actuator assembly 150 is not locked in position by the shutter assembly 160 such that the actuator assembly 150 can move into the actuated position. In the second phase, when the shutter assembly 160 is in the closed configuration, the shutter assembly 160 blocks the laser beam emitted by the laser source and prevents the laser beam from travelling to the distal end. When the shutter assembly 160 is in the open configuration, the shutter assembly 160 allows the laser beam emitted by the laser source to pass through toward distal end.

The actuator assembly 150 can include a base 154 that is supported by the device body 12 as described above. The actuator assembly 150 can further and an assembly body 151 that can also be supported by the device body 112, for instance disposed within the interior cavity 127. In accordance with the illustrated embodiment, the assembly body 151 can be spaced distally from the base 154 along the longitudinal direction L. The actuator assembly 50 can further include a bias member 156, such as a spring, which is coupled between the base 154 and the assembly body 151 along the longitudinal direction L. The bias member provides a spring force that resists movement of the assembly body 151 along the longitudinal direction toward the base 154. The actuator assembly 150 can further include an actuation member 153 that projects distally from the assembly body 151 along the longitudinal direction L. The actuator assembly 150 can further include a rod 89 that is coupled to the assembly body 151 to move along with the assembly body 151. For instance, the rod 89 can be supported by the assembly body 151 and extend from the assembly body 151, or can otherwise be movably coupled to the assembly body 151 as desired. The base 154 can include a body 154a, and an opening 154b that extends at least into or through the body 154a along the longitudinal direction. The opening 154b can be sized to receive the rod 89, such that the rod 89 can extend proximally along the longitudinal direction L relative to the assembly body 151, through the opening 154b, and toward the shutter assembly 160.

The assembly body 151 is movable proximally along the longitudinal direction L relative to the base 154 against the spring force from the bias member 156 so as to close an electronic switch in the above mentioned circuit 300, for example. For instance, as described above with respect to FIGS. 5A-6C, the actuation member 153 is movable proximally along the longitudinal direction L toward the base 154 in response to a proximally directed force F that is applied to the fixation member receiving end 152 of the actuation member 153, for instance at the distal end of the device 110.

The actuator assembly 150 can include an actuator assembly surface 157 that can be defined by a distal-most surface of the assembly body 151. The device body 112 can define a device body surface 123 that faces the actuator assembly surface 157 to define a first distance E1 that extends between the device body surface 123 and the actuator assembly surface 157 along the longitudinal direction. When the actuator assembly 150 is in a first position, the first distance E1 can be equal to about zero, or can be greater than zero. When the actuator assembly 150 is proximally displaced relative to the device body 112 along the longitudinal direction L as described herein, the actuator assembly surface 157 is spaced from the device housing surface 123 along the longitudinal direction L a second distance E2 greater than the first distance E1. The difference between the second distance E2 and the first distance E1 can represent the displacement of the actuator assembly surface 157 relative to the device body 112 that is sufficient to cause the first actuator assembly 150 to move from the first position to the actuated position, and can further cause the rod 89 to move the shutter 160 from the closed position to the open position.

The pathway member 180 includes a pathway body 180a that defines proximal end 184 and a distal end 182 that is spaced distally from the proximal end 184 along the longitudinal direction L. The proximal end 184 can further define an engagement surface 184e configured to engage the shutter assembly 160 as further detailed below. The pathway member 180 can define a bore 186 that extends through the pathway body between the distal end 182 and the proximal end 184, and is aligned with the laser source along the longitudinal direction such that the laser beam travels through the bore 186 when the laser sourced is activated and the shutter 160 is in the closed position. The distal end 182 of the pathway member 180 can translate within actuation member 153. The proximal end 184 of the pathway member 180 is slidable with respect to the base 154 along the longitudinal direction L. For instance, the base 154 can define a second opening 154c that extends at least into or through the body 154a along the longitudinal direction L. The second opening 154c can be sized to receive the proximal end 184 of the pathway member 180, such that the pathway member 180 is movable in the second opening 154c. It should thus be appreciated that the pathway member 180 is displaced in the longitudinal direction L when the fixation member 18 is inserted in the actuation member 53.

A lock member 190 disposed in the base 154 can be used to engage and fix movement of the pathway way member 180. The base body 154a can include a recess 154d in open communication with the base opening 154c such that the pathway member 180 can be engaged by the movable detent 190 disposed in the recess 154d. A bias member 192, which can be a spring, urges the detent 190 in the transverse direction T toward and into contact with the pathway member 180. The pathway member 180 can also include recess 184e disposed on the outer surface on the pathway member 180 in radial alignment with recess 154d, such that when the pathway member 180 is displaced toward the shutter assembly 160, the member recess 193 moves into axial alignment the recess 154d. The bias member 192 pushes the detent 190 at least partially into the corresponding curved recess 193 of the pathway member 180. The detent 190 disposed in the recess 193 can prevent both proximal and distal displacement of the pathway member 180 along the longitudinal direction L.

In accordance with the illustrated embodiment, the shutter assembly 160 can include a shutter body 160b and an aperture 162 that extends through the shutter body 160b along the longitudinal direction L. The shutter body 160b can further define a stop portion 165 that is configured to prevent displacement of the actuator assembly 150. For instance, the stop portion 165 is positioned in alignment with and opposing the rod 89. With the shutter assembly 160 in the locked position as shown FIG. 9A, the stop portion 165 prevents displacement of the actuator assembly 150. The shutter assembly body 160b defines a first engagement surface 160e configured to receive a portion of the pathway member 180, for instance a pathway engagement portion 186e. When the pathway member 180 is displaced from the first position to the second position proximally along the longitudinal direction L, the pathway engagement portion 186e contacts the first engagement surface 160e causing the shutter assembly 160 to move along the transverse direction T from the locked position into the unlocked position.

The shutter body 160b can further define a second engagement surface 160a extending proximally along the longitudinal direction L from the stop portion 165, wherein the second engagement surface 160a is configured to abut and ride along a complementary engagement surface 89a carried by the rod 89 when the stop portion 165 is displaced transversely toward the axis 1. At least one of the engagement surfaces 160a or 89a can be angled, such that movement of the rod 89 along the longitudinal direction L causes the engagement surface 89a to bias the engagement surface 160a, and thus the shutter body 160b, to move along the transverse direction T from the closed configuration to the open configuration. For instance, the movement of the rod 89 can be sufficient to cause the shutter body 160b to move along the transverse direction until the aperture 162 is aligned with the laser source 70 and the pathway member 180, to permit the emitted laser beam to pass into the pathway member 180.

The shutter assembly 160 can further include a first ledge 164b and a second ledge 164a that each extends distally from the shutter body 160b along the longitudinal direction L. The first ledge 164b can be spaced from the second ledge 164a along the transverse direction T such that the shutter assembly 160 defines a recess 163 that extends between the first and second ledges 164a and 164b along the transverse direction T. The first engagement surface 160e can define a portion of the recess 163. The recess 163 can be sized to receive the proximal end 184 of the pathway member 180 when the pathway member 180 is distally displaced (FIG. 9B) and the shutter assembly 160 is in the open position.

The actuator assembly 150 can further include a bias member 166, such as a spring, that extends between the shutter assembly 160 and the base 154 along the transverse direction T. The bias member 166 is configured to provide a biasing force against the shutter assembly 160 that resists movement of the shutter assembly 160 from locking/unlocking positions and from the closed configuration to the open configuration. The bias member 166 retains the shutter assembly 160 in the locked and closed configuration when 1) the pathway member 180 is not disposed in the recess 163, and 2) the rod 89 no longer retains the shutter assembly 160 in the open position. When the shutter assembly 160 is in the locked position, a stop portion 165 of shutter assembly 160 body abuts a portion of the actuator to prevent movement of the actuator 150 from the first position to the actuated position. Further, proximal movement of the rod 89 and corresponding movement of the shutter assembly from the closed configuration to the open configuration can be against the biasing force of the bias member 156.

When the shutter assembly is in the unlocked position as shown in FIG. 9B, the actuation member 153 and assembly body 151 are moveable proximally along the longitudinal direction L from the first position to the actuated position as described above with respect to the actuation member 53 (see FIGS. 4-6C). The engagement surface 89a of the rod 89 is then displaced and bears upon the engagement surface 160a, which causes the shutter assembly 160 to move along the transverse direction T from the closed position shown in FIG. 9B to the open (operable) position shown in FIG. 9C. When the shutter assembly 160 is in the unlocked position, the shutter assembly 160 allows the proximal end 184 of the pathway member 180 to enter into the recess 163, as shown in FIGS. 9B and 9C. Further, when the shutter assembly 160 is in the open configuration, however, the aperture 162 is aligned with the pathway member 180 along the longitudinal direction L and the laser source 70 (FIG. 2D) is positioned proximal to the shutter assembly 160. It should be appreciated that when the actuators of the laser device 110 are in their respective actuated positions, the laser beam can be emitted into the fixation member. For instance, at least one of the actuators can be moved from the respective first position that prevents the laser source 70 from emitting the laser beam to the respective actuated position that no longer prevents the laser source 70 from emitting the laser beam.

Referring to FIGS. 10A-B, in accordance with an alternative embodiment, the laser device 210 can include a laser device body 212 having a distal end 216, and a proximal end 214 spaced apart from a distal end 216 along a longitudinal direction L. The device body 212 can further define a device housing 220 configured to support at least one actuator assembly, similar to the embodiment described above. Further, the laser device 210 can also include a laser 70, power source 90, and at least one circuit 300, which are similar to the embodiment described above and shown in FIGS. 1A-8. In accordance with an alternate embodiment, a shutter assembly 260 that is movable between a first or open position and a second or closed position, and an actuator assembly 250 in operable engagement with a shutter assembly 260 to cause the shutter assembly 260 to move to from the closed position to the open position. When the shutter assembly 260 is in the closed position, the shutter assembly 260 blocks the laser beam emitted by the laser source and prevents the laser beam from travelling to the distal end.

When the shutter assembly 260 is in the open position, the shutter assembly 260 allows the laser beam emitted by the laser source to pass through toward distal end.

The actuator assembly 250 can include a base 254 supported by the device body 212. For instance the base 254 can be disposed stationary within the interior cavity 227 with respect to movement along the longitudinal direction L. The actuator assembly 250 can further and an assembly body 251 supported by the device body 220 within the interior cavity 227. In accordance with the illustrated embodiment, the assembly body 251 can be spaced distally from the base 254 along the longitudinal direction L. The actuator assembly can further include a bias member 256 that is coupled between the base 254 and the assembly body 251 along the longitudinal direction L. The bias member provides a spring force that resists movement of the assembly body 251 along the longitudinal direction toward the base 254. The actuator assembly 250 can further include an actuation member 253 that projects distally from the assembly body 251 along the longitudinal direction L. The actuator assembly 250 includes a rod 289 that is coupled to the assembly body 251 to move along with the assembly body 251. The base 254 can include a body 254a, and an opening 254b that extends at least into or through the body 254a along the longitudinal direction. The opening 254b is sized to receive the rod 289 such that the rod 289 can extend proximally along the longitudinal direction L relative to the assembly body 251 and through the opening 254b toward the shutter assembly 260.

The assembly body 251 is movable proximally along the longitudinal direction L relative to the base 254 against the spring force from the bias member 256 so as to close an electronic switch in the above mentioned circuit 300, for example. For instance, as described above with respect to FIGS. 5A-6C, the actuation member 253 is movable proximally along the longitudinal direction L toward the base 254 in response to a proximally directed force F that is applied to the fixation member receiving end 252 of the actuation member 253. The actuator assembly 250 can include an actuator assembly surface 257 that can be defined by a distal-most surface of the assembly body 151. The device body 212 can define a device body surface 223 that faces the actuator assembly surface 257 to define a first distance F1 that extends between the device body surface 223 and the actuator assembly surface 257 along the longitudinal direction. When the actuator assembly 250 is in a first position, the first distance F1 can be equal to about zero, or can be greater than zero. When the actuator assembly 250 is proximally displaced relative to the device body 212 along the longitudinal direction L as described herein, the actuator assembly surface 157 is spaced from the device housing surface 223 along the longitudinal direction L a second distance F2 that is greater than the first distance F1. The difference between the second distance F2 and the first distance F1 represents the displacement of the actuator assembly surface 257 relative to the device body 212 that is sufficient to cause the first actuator assembly 250 to move from the first position to the actuated position, and can further cause the rod 289 to move the shutter 260 from the closed position to the open position.

The pathway member 280 includes a pathway body 280a that defines proximal end 284 and a distal end 282 that is spaced distally from the proximal end 284 along the longitudinal direction L. The pathway member 280 defines a bore 286 that extends through the pathway body between the distal end 282 and the proximal end 284. The bore 286 is aligned with the laser source along the longitudinal direction such that the laser beam can travel through the bore 286 when the laser sourced is activated and the shutter 260 is in the closed position. The distal end 282 of the pathway member 280 can be translatably fixed to the actuation member 253. Accordingly, movement of the actuation member 253 along the longitudinal direction L causes the pathway member 280 to move with the actuation member 253 along the longitudinal direction L. The proximal end 284 of the pathway member 280 is slidable with respect to the base 254 along the longitudinal direction L. For instance, the base 254 can define a second opening 254c that extends at least into or through the body 254a along the longitudinal direction L. The second opening 254c can be sized to receive the proximal end 284 of the pathway member 280 such that the pathway member 280 is movable in the second opening 254c. It should thus be appreciated that the pathway member 280 is displaced in the longitudinal direction L when the actuation member 253 is displaced as discussed above. The base 254 can include a locking member 290, which is configured similarly to the lock member 190 discussed above and shown in FIGS. 9A-9B.

As described above, movement of the shutter assembly 260 to the open position (FIG. 9A) allows the laser beam emitted by the laser source to travel into the pathway member 280. When the shutter assembly 260 is in the closed position (FIG. 9B), the shutter assembly 260 blocks the laser beam emitted by the laser source and prevents the emitted laser beam from travelling into the pathway member 280. In accordance with the illustrated embodiment, the shutter assembly 260 can include a shutter body 260b and an aperture 262 that extends through the shutter body 260b along the longitudinal direction L. The shutter body 260b can further define an engagement surface 265 that is configured to abut and ride along a complementary engagement surface 289a carried by the rod 289. At least one of the engagement surfaces 265 or 289a can be angled so that movement of the rod 89 along the longitudinal direction L causes the engagement surface 289a to bias the engagement surface 265, and thus the shutter body 260b, to move along the transverse direction T from the closed position to the open position. For instance, the movement of the rod 89 can be sufficient to cause the shutter body 260b to move along the transverse direction T until the aperture 262 is aligned with the laser source 70 and the pathway member 280.

The shutter assembly 260 can further include a first ledge 264a and a second ledge 264b that each extends distally from the shutter body 260b along the longitudinal direction L. The second ledge 264b can be spaced from the first ledge 264a along the transverse direction T such that the shutter assembly 260 defines a recess 263 that extends between the first and second ledges 264a and 264b along the transverse direction T. The recess 263 can be sized to receive the proximal end 284 of the pathway member 280 when the pathway member 280 is distally displaced (see FIG. 10B) and the shutter assembly 260 is in the open position.

The actuator assembly 250 can further include a bias member 256, such as a spring, that extends between the shutter assembly 260 and the base 254 along the transverse direction T. The bias member 256 is configured to provide a biasing force against the shutter assembly 260 that resists movement of the shutter assembly 260 from the closed position to the open position, and retains the shutter assembly 260 in the closed position when the rod 89 does not retain the shutter assembly 260 in the open position. Accordingly, proximal movement of the rod 89 and corresponding movement of the shutter assembly from the closed position to the open position can be against the biasing force of the bias member 256.

The actuation member 253 can be proximally displaced along the longitudinal direction L from the first position to the actuated position as described above with respect to the actuation member 53 (see FIGS. 4-6C). Displacement of the actuation member causes the engagement surface 289a of the rod 289 to displace and bear upon the engagement surface 265, which causes the shutter assembly 260 to move along the transverse direction T from the closed position shown FIG. 10A to the open (operable) position shown in FIG. 10B. When the shutter assembly 260 is in the open position, the shutter assembly 260 allows the proximal end 284 of the pathway member 280 to enter into the recess 263, as shown in FIG. 10B. Further, when the shutter assembly 260 is in the open position, the aperture 262 is aligned with the pathway member 280 along the longitudinal direction L and the laser source 70 (see FIG. 2D) that is position proximal to the shutter assembly 260. It should be appreciated that when the actuators of the laser device 210 are in their respective actuated positions, the laser beam can be emitted into the fixation member. For instance, at least one of the actuators can be moved from the respective first position that prevents the laser source 70 from emitting the laser beam to the respective actuated position that no longer prevents the laser source 70 from emitting the laser beam.

An additional embodiment can include a method for affixing a fixation member to a target surgical location. The method can include the step of engaging a fixation member a fixation member receiving end of a laser device of the type including a laser source and an actuator that is in a first position to prevent the laser source from emitting a laser beam. After the supporting step, the fixation member is inserted at least partially into the target surgical location. During the inserting step, the actuator can be moved from the first position to an actuated position, such that the actuator does not prevent the laser source from emitting the laser beam. Further, the method can include causing the laser source to emit the laser beam to the fixation member, thereby deforming the fixation member in the target surgical location. In additional embodiments of the method, the step of causing the laser source to emit the laser beam to the fixation member is in response to moving step. The method can further include a second step of moving the second actuator from the first position to an actuated position, such that the second actuator does not prevent the laser source from emitting the laser beam. Causing the laser source to emit the laser beam to the fixation member can be in response to the second moving step. The method can also include electrically connecting the power source to the laser source to emit the step of causes the laser source to emit the laser beam to the fixation member. Further, the step of supporting the fixation member on the laser device permits movement of the actuator from the first position to the actuated position.

It should be appreciated that any single component or combination of two or more components as described herein may form exemplary embodiment of the invention. For example, any combination of one, two, or more of the laser device 10 and at least one actuator assembly or circuit 300, and/or shutter assembly 160, 260 may form varying embodiments of the invention. Further, certain features of each of these aforementioned components may be used with the other features of different components as needed.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A fixation member configured to be implanted at a target surgical location, the fixation member comprising:
a fixation member body comprising a polymeric composition and an agent configured to absorb the laser, the fixation member body configured to receive energy from a Class 2, 3, or 4 laser beam and, in response to the received energy from the laser beam, soften at the target surgical location, wherein the fixation member body comprises up to about 2.0% by weight of the agent, and the fixation member body is configured to absorb a sufficient quantity of the received energy so as to emit no more than the energy of a Class 1 laser beam.

2. The fixation member of claim 1, wherein the polymeric composition is blended with the agent.

3. The fixation member of claim 1, wherein a coating of the agent is disposed on the polymeric composition.

4. The fixation member of claim 1, wherein the polymeric composition comprises one or more of polyetheretherketone (PEEK), polyetherketoneketone (PEKK), polylactic acid (PLA), polyglocolic acid (PGA), Polyglycolic-Lactic Acid (PGLA), polymethyl methacrylate (PMMA), and polycaprolactone (PCL).

5. The fixation member claim 1, wherein the fixation member body comprises about 0.75% by weight of the agent.

6. The fixation member of claim 1, wherein the agent includes Blue No. 6.

7. The fixation member of claim 1, wherein the fixation member body has a trailing end and an insertion end spaced from the trailing along a fixation member axis, wherein the trailing end defines a structure configured to engage with a laser device that is configured to emit a laser beam.

8. The fixation member claim 7, wherein, when the fixation member is engaged with the laser device, the laser device and the fixation member are configured to enclose the laser beam such that the laser beam is not visible to a user when the laser device emits the laser beam.

9. The fixation member of claim 1, wherein the fixation member body has a proximal end and a distal end spaced from the proximal end along a longitudinal direction, and the fixation member body defines a cannulation that extends from the proximal end toward the distal end along the longitudinal direction.

10. A fixation member configured to be implanted at a target surgical location, the fixation member comprising:
a fixation member body that is configured to receive energy from a Class 2, 3, or 4 laser beam and, in response to the received energy from the laser beam, soften at the target surgical location, the fixation member body configured to absorb a sufficient quantity of the received energy so as to emit no more than the energy of a Class 1 laser beam, wherein the fixation member body has a trailing end and an insertion end spaced from the trailing along a fixation member axis, wherein the trailing end defines a structure configured to engage with a laser device that is configured to emit a laser beam, and wherein the trailing end of the fixation member includes a head, a ridge spaced distally from the head along the fixation member axis, and a neck disposed between the head and the ridge.

11. The fixation member of claim 10, wherein the head defines a first cross-sectional dimension, the neck defines a second cross-sectional dimension, and the ridge defines a third cross-sectional dimension, wherein the second cross-sectional dimension is less than at least one of the first cross-sectional dimension and the third cross-sectional dimension.

12. The fixation member of claim 11, wherein the second cross-sectional dimension is less than both the first cross-sectional dimension and the third cross-sectional dimension.

13. The fixation member of claim 10, wherein the fixation member body comprises a polymeric composition and an agent configured to absorb the laser.

14. The fixation member of claim 13, wherein the polymeric composition comprises one or more of polyetheretherketone (PEEK), polyetherketoneketone (PEKK), polylactic acid (PLA), polyglocolic acid (PGA), Polyglycolic-Lactic Acid (PGLA), polymethyl methacrylate (PMMA), and polycaprolactone (PCL).

15. The fixation member of claim 13, wherein the agent includes Blue No. 6.

16. A method of implanting a fixation member at a target surgical location, the method comprising steps of:

receiving energy from a Class 2, 3, or 4 laser beam at a fixation member body of the fixation member so as to soften the fixation member body at the target surgical location;
absorbing a quantity of the energy by the fixation member body; and
emitting no more than the energy of a Class 1 laser beam from the fixation member body in response to the absorbing step.

17. The method of claim 16, comprising a step of engaging, before the transmitting step, a trailing end of the fixation member body with a laser device that is configured to emit the laser beam.

18. The method of claim 17, wherein the engaging step comprises enclosing the laser beam with the laser device and the fixation member such that the laser beam is not visible to a user when the laser device emits the laser beam.

19. The method of claim 17, wherein the engaging step comprises receiving a portion of the laser device in a cannulation that extends from a proximal end of the fixation member body toward a distal end of the fixation member body.

20. The method of claim 16, comprising a step of reducing the energy that is received by the fixation member body from the Class 2, 3, or 4 laser beam to the energy of the Class 1 laser beam.

* * * * *